(12) United States Patent
Hale et al.

(10) Patent No.: US 7,183,307 B2
(45) Date of Patent: *Feb. 27, 2007

(54) PYRAZOLE-DERIVED KINASE INHIBITORS AND USES THEREOF

(75) Inventors: Michael Robin Hale, Bedford, MA (US); James Walter Janetka, Beverly, MA (US); Francois Maltais, Tewksbury, MA (US); Qing Tang, Cambridge, MA (US)

(73) Assignee: Vertex Pharmaceuticals Incroporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/837,848

(22) Filed: May 3, 2004

(65) Prior Publication Data

US 2004/0209935 A1    Oct. 21, 2004

Related U.S. Application Data

(62) Division of application No. 10/212,294, filed on Aug. 2, 2002, now Pat. No. 6,750,239.

(60) Provisional application No. 60/309,865, filed on Aug. 3, 2001.

(51) Int. Cl.
*A61K 31/415*    (2006.01)
*C07D 231/02*    (2006.01)

(52) U.S. Cl. .................................. 514/406; 548/364.1

(58) Field of Classification Search ............. 548/364.1; 514/406

See application file for complete search history.

(56) References Cited

U.S. PATENT DOCUMENTS

| | | | |
|---|---|---|---|
| 5,837,719 A | 11/1998 | De Laszio et al. | |
| 6,087,496 A | 7/2000 | Anantanarayan et al. | |
| 6,528,509 B1 * | 3/2003 | Hale et al. | 514/236.5 |
| 6,593,357 B1 * | 7/2003 | Green et al. | 514/406 |
| 6,699,865 B2 * | 3/2004 | Hale et al. | 514/236.5 |
| 6,750,239 B2 * | 6/2004 | Hale et al. | 514/406 |

FOREIGN PATENT DOCUMENTS

| WO | WO 98 52941 A | 11/1998 |
|---|---|---|
| WO | WO 01 57022 A | 8/2001 |

OTHER PUBLICATIONS

Ambiter, "Screening collection (catalog)"; Abstract, CAS Registry No. 321553-20-2; Aug. 23, 1999.

* cited by examiner

*Primary Examiner*—Joseph K. McKane
*Assistant Examiner*—Robert Shiao
(74) *Attorney, Agent, or Firm*—Karen E. Brown; Daniel A. Pearson; Vertex Pharmaceuticals Incorporated

(57) ABSTRACT

Described herein are compounds that are useful as protein kinase inhibitors having the formula:

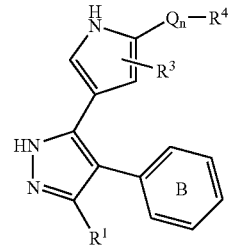

wherein B, $R^1$, n, $R^3$, Q and $R^4$ are described in the specification. The compounds are useful for treating disease states in mammals that are alleviated by a protein kinase inhibitor, particularly diseases such as cancer, inflammatory disorders, restenosis, and cardiovascular disease.

7 Claims, No Drawings

PYRAZOLE-DERIVED KINASE INHIBITORS AND USES THEREOF

CROSS-REFERENCE TO RELATED APPLICATIONS

This application is a divisional of U.S. patent application Ser. No. 10/212,294, filed Aug. 2, 2002 now U.S. Pat. No. 6,750,239, which claims priority to U.S. Provisional Application Ser. No. 60/309,865, filed Aug. 3, 2001, the entirety of which is incorporated herein by reference.

TECHNICAL FIELD OF THE INVENTION

The present invention is in the field of medicinal chemistry and relates to pyrazole compounds that are protein kinase inhibitors, especially inhibitors of ERK, compositions containing such compounds and methods of use. The compounds are useful for treating cancer and other disease states that are alleviated by protein kinase inhibitors.

BACKGROUND OF THE INVENTION

Mammalian mitogen-activated protein (MAP) kinases are serine/threonine kinases that mediate intracellular signal transduction pathways (Cobb and Goldsmith, 1995, *J Biol. Chem.*, 270, 14843; and Davis, 1995, *Mol. Reprod. Dev.* 42, 459). Members of the MAP kinase family share sequence similarity and conserved structural domains, and include the ERK (extracellular signal regulated kinase), JNK (Jun N-terminal kinase), and p38 kinases. JNKs and p38 kinases are activated in response to the pro-inflammatory cytokines TNF-alpha and interleukin-1, and by cellular stress such as heat shock, hyperosmolarity, ultraviolet radiation, lipopolysaccharides and inhibitors of protein synthesis (Derijard et al., 1994, *Cell* 76, 1025; Han et al., 1994, *Science* 265, 808; Raingeaud et al., 1995, *J Biol. Chem.* 270, 7420; and Shapiro and Dinarello, 1995, *Proc. Natl. Acad. Sci. USA* 92, 12230). In contrast, ERKs are activated by mitogens and growth factors (Bokemeyer et al. 1996, *Kidney Int.* 49, 1187).

ERK2 is a widely distributed protein kinase that achieves maximum activity when both Thr183 and Tyr185 are phosphorylated by the upstream MAP kinase kinase, MEK1 (Anderson et al., 1990, *Nature* 343, 651; and Crews et al., 1992, *Science* 258, 478). Upon activation, ERK2 phosphorylates many regulatory proteins, including the protein kinases Rsk90 (Bjorbaek et al., 1995, *J. Biol. Chem.* 270, 18848) and MAPKAP2 (Rouse et al., 1994, *Cell* 78, 1027), and transcription factors such as ATF2 (Raingeaud et al., 1996, *Mol. Cell Biol.* 16, 1247), Elk-1 (Raingeaud et al. 1996), c-Fos (Chen et al., 1993 *Proc. Natl. Acad. Sci. USA* 90, 10952), and c-Myc (Oliver et al., 1995, *Proc. Soc. Exp. Biol. Med.* 210, 162). ERK2 is also a downstream target of the Ras/Raf dependent pathways (Moodie et al., 1993, *Science* 260, 1658) and may help relay the signals from these potentially oncogenic proteins. ERK2 has been shown to play a role in the negative growth control of breast cancer cells (Frey and Mulder, 1997, *Cancer Res.* 57, 628) and hyperexpression of ERK2 in human breast cancer has been reported (Sivaraman et al., 1997, *J Clin. Invest.* 99, 1478). Activated ERK2 has also been implicated in the proliferation of endothelin-stimulated airway smooth muscle cells, suggesting a role for this kinase in asthma (Whelchel et al., 1997, *Am. J. Respir. Cell Mol. Biol.* 16, 589).

AKT, also known as protein kinase B, is a serine/threonine kinase that plays a central role in promoting the survival of a wide range of cell types (Khwaja, A., 1990, *Nature, pp.* 33–34). It has been shown by Zang et al. that human ovarian cancer cells display elevated levels of AKT-1 and AKT-2. Inhibition of AKT induces apoptosis of these human ovarian cancer cells which demonstrates that AKT may be an important target for ovarian cancer treatment (Zang, Q. Y. et al., 2000, *Oncogene,* 19) and other proliferative disorders. The AKT pathway has also been implicated in motoneuronal survival and nerve regeneration (Kazuhiko, N. et al., 2000, *The Journal of Neuroscience,* 20).

A number of compounds have been developed that purport to specifically inhibit various MAPKs. PCT publication WO 95/31451 describes pyrazole derivatives that inhibit p38. However, it is not clear whether these compounds have the appropriate pharmacological profiles to be therapeutically useful.

Aryl-substituted pyrroles are known in the literature. In particular, tri-aryl pyrroles (U.S. Pat. No. 5,837,719) have been described as having glucagon antagonist activity. 1,5-Diarylpyrazoles have been described as p38 inhibitors (WO 99/58523).

There is a high unmet medical need to develop new therapeutic treatments that are useful in treating the various conditions associated with ERK activation. For many of these conditions the currently available treatment options are inadequate.

Accordingly, there is great interest in new and effective inhibitors of protein kinase, including ERK inhibitors, which are useful in treating various conditions associated with protein kinase activation.

SUMMARY OF THE INVENTION

The present invention provides novel classes of compounds, and pharmaceutically acceptable derivatives thereof, that are useful as protein kinase inhibitors. These compounds can be used alone or in combination with other therapeutic or prophylactic agents, such as antibiotics, immunomodulators or other anti-inflammatory agents, for the treatment or prophylaxis of diseases mediated by protein kinases, including ERK and AKT. According to a preferred embodiment, the compounds of this invention are capable of binding to the active site of ERK or AKT and inhibiting the activity of that enzyme.

It is a principal object of this invention to provide novel classes of compounds that are protein kinase inhibitors represented by formula I:

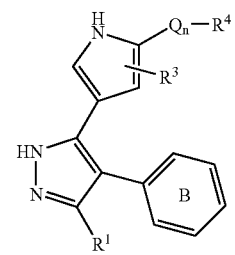

or a pharmaceutically acceptable derivative thereof, wherein

B is a phenyl ring having a substituent -L-A and 0–3 $R^2$ substituents;

L is an optionally substituted $C_1$–$C_6$ alkylidene chain; wherein at least 1 and optionally up to 2 methylene units are replaced by —O—, —C(O)—, —C(O)C(O)—, —C(O)

—NR$^8$—, —C(O)NR$^8$NR$^8$—, —CO$_2$—, —OC(O)—, —NR$^8$CO$_2$—, —NR$^8$C(O)NR$^8$—, —OC(O)NR$^8$—, —NR$^8$—, —NR$^8$NR$^8$—, —NR$^8$CO—, —S—, —SO—, —SO$_2$—, —SO$_2$NR$^8$—, —NR$^8$SO$_2$—, —NR$^8$SO$_2$NR$^8$—, —N(R$^8$)O—, or —ON(R$^8$)—;

A is

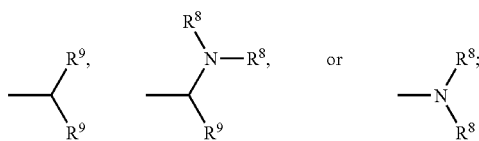

Q is an optionally substituted C$_1$–C$_6$ alkylidene chain, wherein up to two methylene units are replaced by —C(O)—, —C(O)C(O)—, —C(O)NR$^7$—, —C(O)NR$^7$NR$^7$—, —CO$_2$—, —OC(O)—, —NR$^7$CO$_2$—, —O—, —NR$^7$C(O)NR$^7$—, —OC(O)NR$^7$—, —NR$^7$NR$^7$—, —NR$^7$C(O)—, —S—, —SO—, —SO$_2$—, —NR$^7$—, —SO$_2$NR$^7$—, —NR$^7$SO$_2$—, or —NR$^7$SO$_2$NR$^7$—;

n is zero or one;

R$^1$ is hydrogen, R, fluoro, —CN, N(R$^7$)$_2$, OR$^7$, NR$^7$C(O)R$^7$, NR$^7$C(O)N(R$^7$)$_2$, C(O)N(R$^7$)$_2$, SO$_2$R$^7$, NR$^7$SO$_2$R$^7$, or SO$_2$N(R$^7$)$_2$;

each R$^2$ is independently selected from R, OH, OR, SH, SR, nitro, N(R$^7$)$_2$, halogen, CF$_3$, or cyano;

R$^3$ is hydrogen, R, OH, OR, N(R$^7$)$_2$, fluoro, or CN;

R$^4$ is selected from —(CH$_2$)$_y$R$^6$, —(CH$_2$)$_y$R$^{10}$, —(CH$_2$)$_y$CH(R$^6$)$_2$, —(CH$_2$)$_y$CH(R$^{10}$)$_2$, —(CH$_2$)$_y$CH(R$^{10}$)CH(R$^6$)$_2$, —(CH$_2$)$_y$CH(R$^{10}$)(R$^6$), —N(R$^5$)$_2$, or —NR$^5$(CH$_2$)$_y$N(R$^5$)$_2$;

each R is independently selected from an optionally substituted group selected from C$_{1-6}$ aliphatic, C$_{6-10}$ aryl, heteroaryl having 5–10 ring atoms, or heterocyclyl having 3–10 ring atoms;

each R$^5$ is independently selected from R, —(CH$_2$)$_y$R$^6$, —(CH$_2$)$_y$CH(R$^6$)$_2$, R$^7$, —C(O)R$^7$, —CO$_2$R$^7$, —C(O)N(R$^7$)$_2$, or —SO$_2$R$^7$;

each y is independently 0–6;

each R$^6$ is independently selected from hydrogen, R, —(CH$_2$)$_y$R, —OH, —OR, —CO$_2$R, —(CH$_2$)$_y$N(R$^7$)$_2$, —N(R$_7$)$_2$, —OR$^7$, —SR$^7$, —NR$^7$C(O)R$^7$, —NR$^7$C(O)N(R$^7$)$_2$, —C(O)N(R$^7$)$_2$, —SO$_2$R$^7$, —NR$^7$SO$_2$R$^7$, —C(O)R$^7$, —CN, or —SO$_2$N(R$^7$)$_2$;

each R$^7$ is independently selected from hydrogen or an optionally substituted C$_{1-6}$ aliphatic-group, or two R$^7$ on the same nitrogen are taken together with the nitrogen to optionally form a 5–8 membered heterocyclic or heteroaryl ring;

each R$^8$ is independently selected from hydrogen, R, —(CH$_2$)$_y$R$^9$, —(CH$_2$)$_y$CH(R$^9$)$_2$, —(CH$_2$)$_y$C(O)R$^9$, R$^9$, or R$^7$;

each R$^9$ is independently selected from hydrogen, R, —OH, —OR, —SR, —S(O)R, —SO$_2$R, —C(O)R$^6$, —CO$_2$R$^6$, NR$_2$, halo, cyano, or nitro;

each R$^{10}$ is independently selected from R, —(CH$_2$)$_w$OR$^7$, —(CH$_2$)$_w$N(R$^5$)$_2$, or —(CH$_2$)$_w$SR$^7$; and each w is independently 0–4;

provided that when Q$_n$-R$^4$ is

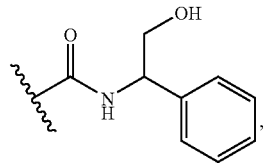

R$^1$ is H, and R$^3$ is H, and R$^2$ is a meta substituent Cl, then -L-A is not a para substituent

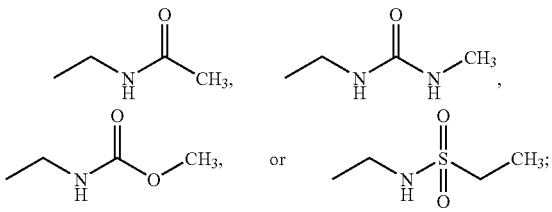

and when Q$_n$-R$^4$ is

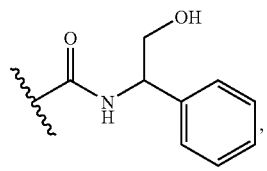

R$^1$ is NH$_2$, R$^2$ is a meta substituent Cl, and R$^3$ is H, then -L-A is not a para substituent

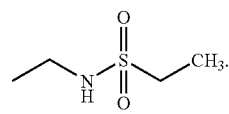

It is a further objective of this invention to provide pharmaceutical compositions comprising the protein kinase inhibitors of this invention. In a preferred embodiment, the protein kinase inhibitors inhibit ERK. These compositions may be utilized in methods for treating or preventing a variety of protein kinase-mediated disorders, such as cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. Each of the above-described methods is also part of the present invention.

It is a further objective of this invention to provide methods for making the compounds and compositions of this invention.

DETAILED DESCRIPTION OF THE INVENTION

The present invention relates to compounds of Formula I. Accordingly, it has now been found that compounds of this invention and compositions thereof are effective as protein kinase inhibitors, especially as inhibitors of ERK2.

As used herein, the following definitions shall apply unless otherwise indicated. The phrase "optionally substituted" is used interchangeably with the phrase "substituted or unsubstituted." Unless otherwise indicated, an optionally substituted group may have a substituent at each substitutable position of the group, and each substitution is independent of any other. Also, combinations of substituents or variables are permissible only if such combinations result in stable compounds. In addition, unless otherwise indicated, functional group radicals are independently selected.

The term "aliphatic" or "aliphatic group" as used herein means a straight-chain or branched $C_1$–$C_{12}$ hydrocarbon chain that is completely saturated or that contains one or more units of unsaturation, or a monocyclic $C_3$–$C_8$ hydrocarbon or bicyclic $C_8$–$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3–7 members. For example, suitable aliphatic groups include, but are not limited to, linear or branched or alkyl, alkenyl, alkynyl groups and hybrids thereof such as (cycloalkyl)alkyl, (cycloalkenyl) alkyl or (cycloalkyl)alkenyl.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 1–3 heteroatoms selected from oxygen, sulfur or nitrogen, the nitrogen may be N (as in 3,4-dihydro-2H-pyrrolyl), NH (as in pyrrolidinyl) or NR$^+$ (as in N-substituted pyrrolidinyl).

The term "aryl" used alone or in combination with other terms, refers to monocyclic, bicyclic or tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring". The term "aralkyl" refers to an alkyl group substituted by an aryl. The term "aralkoxy" refers to an alkoxy group substituted by an aryl.

The term "heterocycle", "heterocyclyl", or "heterocyclic" as used herein means monocyclic, bicyclic or tricyclic ring systems having five to fourteen ring members in which one or more ring members is a heteroatom, wherein each ring in the system contains 3 to 7 ring members and is non-aromatic.

The term "heteroaryl", used alone or in combination with other terms, refers to monocyclic, bicyclic and tricyclic ring systems having a total of five to fourteen ring members, and wherein: 1) at least one ring in the system is aromatic; 2) at least one ring in the system contains one or more heteroatoms; and 3) each ring in the system contains 3 to 7 ring members. The term "heteroaryl" may be used interchangeably with the term "heteroaryl ring" or the term "heteroaromatic". The term "heteroaralkyl" refers to an alkyl group substituted by a heteroaryl. The term "heteroarylalkoxy" refers to an alkoxy group substituted by a heteroaryl.

An aryl (including aralkyl, aralkoxy, aryloxyalkyl and the like) or heteroaryl (including heteroaralkyl, heteroarylalkoxy and the like) group may contain one or more substituents. Suitable substituents on the unsaturated carbon atom of an aryl, heteroaryl, aralkyl, or heteroaralkyl group are selected from halogen; haloalkyl; —CF$_3$; —R°; —OR°; —SR°; 1,2-methylene-dioxy; 1,2-ethylenedioxy; protected OH (such as acyloxy); phenyl (Ph); Ph substituted with R°; —O(Ph); —O-(Ph) substituted with R°; —CH$_2$(Ph); —CH$_2$(Ph) substituted with R°; —CH$_2$CH$_2$(Ph); —CH$_2$CH$_2$(Ph) substituted with R°; —NO$_2$; —CN; —N(R°)$_2$; —NR°C(O) R°; —NR°C(O)N(R°)$_2$; —NR°CO$_2$R°; —NR°NR°C(O)R°; —NR°NR°C(O)N(R°)$_2$; —NR°NR°CO$_2$R°; —C(O)C(O) R°; —C(O)CH$_2$C(O)R°; —CO$_2$R°; —C(O)R°; —C(O)N (R°)$_2$; —OC(O)N(R°)$_2$; —S(O)$_2$R°; —SO$_2$N(R°)$_2$; —S(O) R°; —NR°SO$_2$N(R°)$_2$; —NR°SO$_2$R°; —C(=S)N(R°)$_2$; —C(=NH)—N(R°)$_2$; —(CH$_2$)$_y$NHC(O)R°; —(CH$_2$)$_y$R°; —(CH$_2$)$_y$NHC(O)NHR°; —(CH$_2$)$_y$NHC(O)OR°; —(CH$_2$)$_y$ NHS(O)R°; —(CH$_2$)$_y$NHSO$_2$R°; or —(CH$_2$)$_y$NHC(O)CH ((V)$_z$—R°)(R°), wherein each R° is independently selected from hydrogen, optionally substituted $C_{1-6}$ aliphatic, an unsubstituted 5–6 membered heteroaryl-or heterocyclic ring, phenyl (Ph), —O(Ph), or —CH$_2$(Ph)-CH$_2$(Ph), wherein y is 0–6; z is 0–1; and V is a linker group. When R° is $C_{1-6}$ aliphatic, it may be substituted with one or more substituents selected from —NH$_2$, —NH(C$_{1-4}$ aliphatic), —N(C$_{1-4}$ aliphatic)$_2$, —S (O)(C$_{1-4}$ aliphatic), —SO$_2$(C$_{1-4}$ aliphatic), halogen, —(C$_{1-4}$ aliphatic), —OH, —O—(C$_{1-4}$ aliphatic), —NO$_2$, —CN, —CO$_2$H, —CO$_2$(C$_{1-4}$ aliphatic), —O(halo C$_{1-4}$ aliphatic), or -halo(C$_{1-4}$ aliphatic); wherein each C$_{1-4}$ aliphatic is unsubstituted.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$ (alkyl), or =NR*, where each R* is independently selected from hydrogen or an optionally substituted C$_{1-6}$ aliphatic. When R* is C$_{1-6}$ aliphatic, it may be substituted with one or more substituents selected from —NH$_2$, —NH(C$_{1-4}$ aliphatic), —N(C$_{1-4}$ aliphatic)$_2$, halogen, —OH, —O—(C$_{1-4}$ aliphatic), —NO$_2$, —CN, —CO$_2$H, —CO$_2$(C$_{1-4}$ aliphatic), —O(halo C$_{1-4}$ aliphatic), or -halo(C$_{1-4}$ aliphatic); wherein each C$_{1-4}$ aliphatic is unsubstituted.

Substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein each R$^+$ is independently selected from hydrogen, an optionally substituted C$_{1-6}$ aliphatic, optionally substituted phenyl (Ph), optionally substituted —O(Ph), optionally substituted —CH$_2$(Ph), optionally substituted —CH$_2$CH$_2$(Ph), or an unsubstituted 5–6 membered heteroaryl or heterocyclic ring. When R$^+$ is a C$_{1-6}$ aliphatic group or a phenyl ring, it may be substituted with one or more substituents selected from —$NH_2$, —$NH(C_{1-4}$ aliphatic), —$N(C_{1-4}$ aliphatic)$_2$, halogen, —$(C_{1-4}$ aliphatic), —OH, —O—$(C_{1-4}$ aliphatic), —$NO_2$, —CN, —$CO_2H$, —$CO_2(C_{1-4}$ aliphatic), —O(halo $C_{1-4}$ aliphatic), or -halo $(C_{1-4}$ aliphatic); wherein each $C_{1-4}$ aliphatic is unsubstituted.

The term "linker group" or "linker" means an organic moiety that connects two parts of a compound. Linkers comprise alkylidene chain that is a saturated or unsaturated, straight or branched, $C_{1-8}$ carbon chain which is optionally substituted, and wherein up to two non-adjacent saturated carbons of the chain are optionally replaced by —C(O)—, —C(O)C(O)—, —C(O)NR*—, —C(O)NR*NR*—, —$CO_2$—, —OC(O)—, —NR*$CO_2$—, —O—, —NR*C(O)NR*—, —OC(O)NR*—, —NR*NR*—, —NR*C(O)—, —S—, —SO—, —$SO_2$—, —NR*—, —$SO_2$NR*—, or —NR*$SO_2$—; wherein R* is selected from hydrogen or $C_{1-4}$ aliphatic; wherein $C_{1-4}$ aliphatic is unsubstituted. Optional substituents on the alkylidene chain are as described above for an aliphatic group.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention.

One embodiment of this invention relates to a compound of formula I:

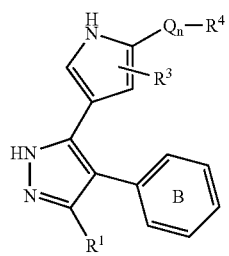

I or a pharmaceutically acceptable derivative thereof, wherein B, $R^1$, $R^3$, Q, n and $R^4$ are as described above.

Another embodiment of this invention relates to compounds wherein B is substituted with one $R^2$ and wherein A is

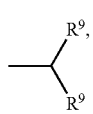

(II-A)

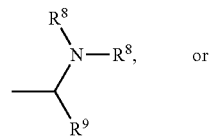

(II-B)

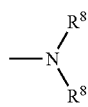

(II-C)

as shown below:

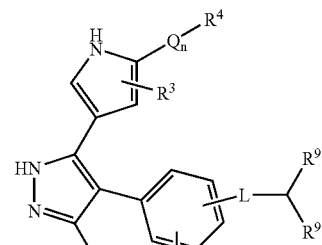

II-A

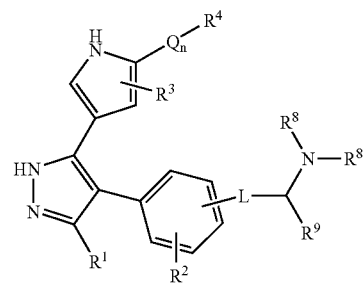

II-B

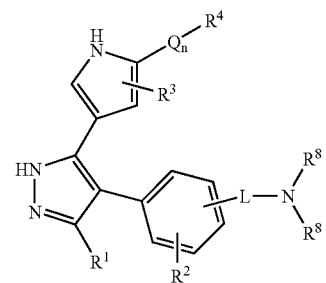

II-C or a pharmaceutically acceptable derivative thereof, wherein $R^1$, n, $R^3$, Q, $R^4$, L, $R^2$, $R^8$, and $R^9$ are as described above.

Preferred compounds of formulae II-A, II-B, and II-C are those having one or more, and most preferably all, of the features selected from the group consisting of: (a) Q is —CO—, —$CO_2$—, or —CONH—; (b) $R^1$ is hydrogen or $NHR^7$; (c) $R^2$ is a meta substituent on the phenyl ring; (d) -L-A is a para substituent on the phenyl ring; (e) $R^4$ is —$NR^5(CH_2)_yN(R^5)_2$, —$(CH_2)_yR^6$, —$(CH_2)_yCH(R^6)_2$, —$(CH_2)_yCH(R^{10})CH(R^6)_2$, —$(CH_2)_yCH(R^{10})$ $(R_6)$, —$(CH_2)_yCH(R^{10})$, or —$(CH_2)_yCH(R^{10})_2$; (f) $R^5$ is R, $R^7$ or —$(CH_2)_yCH(R^6)_2$; and (g) each $R^6$ is an optionally substituted group selected from $C_{1-6}$ aliphatic, phenyl, 5–6 membered heteroaryl, or 5–6 membered heterocyclyl.

More preferred compounds of formulae II-A, II-B, and II-C are those having one or more, and most preferably all, of the following features: (a) $R^2$ is halogen, nitrile, or $CF_3$; (b) one methylene unit of L is replaced; and (c) L is replaced with —NH—, —NHC(O)—, or —C(O)NH—.

When $R^4$ is $R^6$, examples of preferred $R^6$ groups are selected from pyrrolidin-1-yl, morpholin-1-yl, piperidin-1-yl, and piperazin-1-yl wherein each group is optionally substituted. When $R^4$ is $(CH_2)_y R^{10}$, or $(CH_2)_y CH(R^{10})_2$, additional preferred $R^{10}$ groups are selected from pyridin-3-yl, pyridin-4-yl, imidazolyl, furan-2-yl, 1,2,3,4-tetrahydroisoquinoline, tetrahydrofuran-2-yl, cyclohexyl, phenyl, benzyl, —$CH_2OH$, —$(CH_2)_2OH$, and isopropyl, wherein each group is optionally substituted.

Preferred substituents on $R^6$ or $R^{10}$ are selected from —OH, pyridyl, piperidinyl, or optionally substituted phenyl.

More preferred embodiments of this invention are represented by formulae III-A, III-B, and III-C:

or a pharmaceutically acceptable derivative thereof, wherein $R^8$, $R^9$, y, $R^1$, $R^2$, n, $R^3$, Q and $R^4$ are as described above; and wherein W is O or $H_2$;

Z is an optionally substituted $C_1$–$C_4$ alkylidene chain; wherein 1 methylene unit is optionally replaced by —O—, —C(O)—, —C(O)C(O)—, —C(O)NH—, —C(O)NHNH—, —$CO_2$—, —OC(O)—, —$NHCO_2$—, —NHC(O)NH—, —OC(O)NH—, —NH—, —NHNH—, —NHCO—, —S—, —SO—, —$SO_2$—, —$SO_2NH$—, —$NHSO_2$—, or —$NHSO_2NH$—; and m is 0 or 1.

Preferred compounds of formulae III-A, III-B, and III-C are as described above for compounds of formulae II-A, II-B, and II-C.

Additional preferred embodiments relate to compounds of formulae IV-A, IV-B, and IV-C:

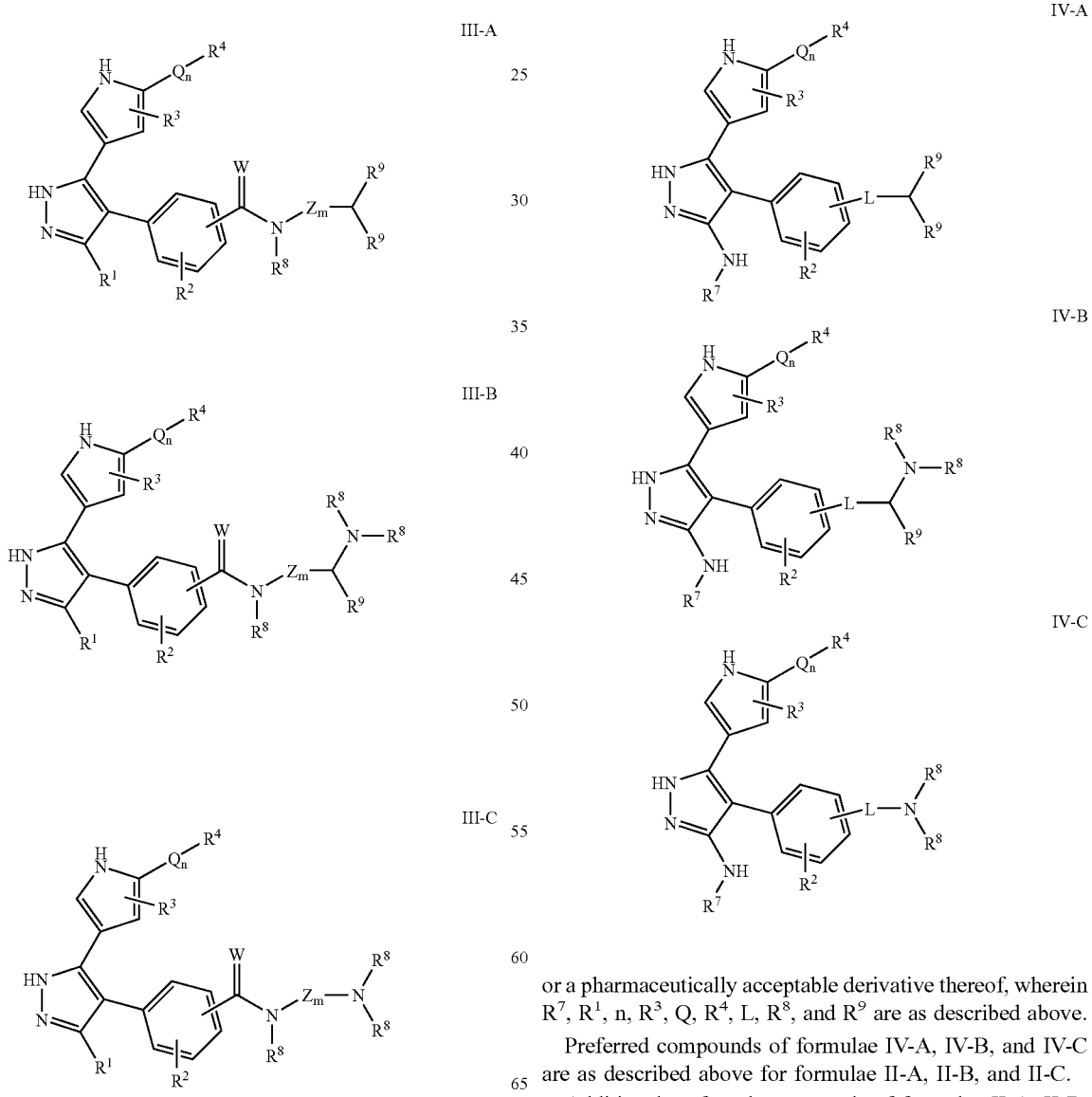

or a pharmaceutically acceptable derivative thereof, wherein $R^7$, $R^1$, n, $R^3$, Q, $R^4$, L, $R^8$, and $R^9$ are as described above.

Preferred compounds of formulae IV-A, IV-B, and IV-C are as described above for formulae II-A, II-B, and II-C.

Additional preferred compounds of formulae II-A, II-B, II-C are those of formulae II-A', II-B', and II-C':

II-A′

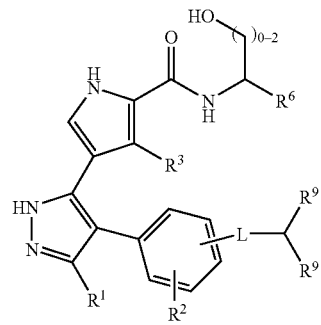

II-B′

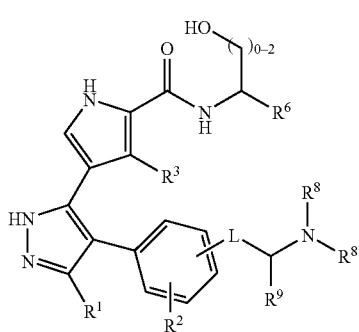

II-C′

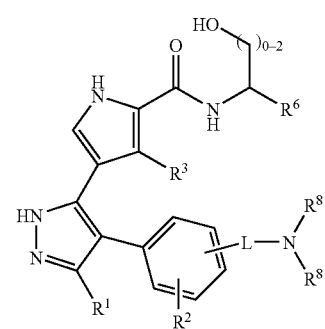

Preferred compounds of formulae II-A, II-B, and II-C are further selected from those of formulae II-A′, II-B′, and II-C′:

II-A°

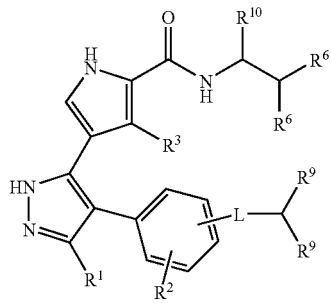

II-B°

II-C°

Preferred R⁶ groups of formulae II-A′, II-B′, and II-C′ are optionally substituted 6-membered aryl, heteroaryl, and carbocyclic rings, such as phenyl, pyridyl, and cyclohexyl. More preferred R⁶ groups are optionally substituted cyclohexyl, 6-membered aryl and heteroaryl. Even more preferred R⁶ groups are cyclohexyl or an optionally substituted phenyl or pyridyl ring.

Preferred R¹ and R² groups of formulae II-A′, II-B′, and II-C′ are as described above for formulae II-A, II-B, and II-C.

Preferred R⁶ groups of formulae II-A°, II-B°, and II-C° are R or OR⁷. Examples of such groups are OH, CH₂OH, or optionally substituted 6-membered aryl, heteroaryl, and carbocyclic rings, such as phenyl, pyridyl, and cyclohexyl. Preferred R¹⁰ groups of formulae II-A°, II-B°, and II-C° are R and OR⁷, wherein R is an optionally substituted group selected from C₁₋₄ aliphatic, 3–6 membered heterocyclic, or a 5–6 membered aryl or heteroaryl ring. Examples of such groups are phenyl, methyl, ethyl, OH, and CH₂OH.

Exemplary structures of formula II-A, II-B, and II-C wherein the phenyl ring is substituted with one R² at the 3-position unless otherwise indicated, R¹ is H, R³ is H, n is one, and -L-A is at the 4-position unless otherwise indicated are set forth in Table 1 below.

TABLE 1

Compounds II-A, II-B, and II-C

| No. | R² | —L—A | Qₙ—R⁴ |
|---|---|---|---|
| II-1 | Cl | —NHC(O)CH₂S(O)₂CH₃ | —C(O)NH—CH(CH₂OH)(phenyl) |
| II-2 | Cl | —CH₂NHS(O)₂CH₃ | —C(O)NH—CH(CH₂OH)(phenyl) |
| II-3 | Cl | —NHC(O)CH₂CH₂OCH₃ | —C(O)NH—CH(CH₂OH)(phenyl) |
| II-4 | Cl | —NHC(O)CH₂CH₂OH | —C(O)NH—CH(CH₂OH)(phenyl) |
| II-5 | Cl | —NHC(O)CH(NHC(O)CH₃)CH₂CH₂OH | —C(O)NH—CH(CH₂OH)(3-Cl-4-F-phenyl) |
| II-6 | Cl | —NHC(O)CH₂S(O)CH₃ | —C(O)NH—CH(CH₂OH)(3-Cl-4-F-phenyl) |
| II-7 | Cl | —CH₂NHCH₂CH₂CH₃ | —C(O)NH—CH(CH₂OH)(3-Cl-4-F-phenyl) |
| II-8 | Cl | —CH₂NHC(O)CH₂CH₂CH₂OH | —C(O)NH—CH(CH₂OH)(3-Cl-4-F-phenyl) |

TABLE 1-continued

Compounds II-A, II-B, and II-C

| No. | R² | —L—A | Qₙ—R⁴ |
|---|---|---|---|
| II-9 | Cl | (structure: -NH-C(=O)-CH(CH₂OH)-NH-C(=O)-CH₃) | (structure: -C(=O)-NH-CH(CH₂OH)-(3-Cl,4-F-phenyl)) |
| II-10 | Cl | (structure: -NH-C(=O)-CH(CH₃)-NH-C(=O)-CH₃) | (structure: -C(=O)-NH-CH(CH₂OH)-(3-Cl,4-F-phenyl)) |
| II-11 | Cl | (structure: -NH-C(=O)-CH(CH₃)-NH-C(=O)-CH₃, opposite stereochem) | (structure: -C(=O)-NH-CH(CH₂OH)-(3-Cl,4-F-phenyl)) |
| II-12 | Cl | (structure: -NH-C(=O)-CH(CH₂SH)-NH-C(=O)-CH₃) | (structure: -C(=O)-NH-CH(CH₂OH)-(3-Cl,4-F-phenyl)) |
| II-13 | Cl | (structure: -NH-C(=O)-CH₂-N(CH₃)₂) | (structure: -C(=O)-NH-CH(CH₂OH)-(3-Cl,4-F-phenyl)) |
| II-14 | Cl | (structure: -NH-C(=O)-CH(CH₂OH)-NH-C(=O)-O-C(CH₃)₃) | (structure: -C(=O)-NH-CH(CH₂OH)-(3-Cl,4-F-phenyl)) |
| II-15 | Cl | (structure: -NH-C(=O)-CH(CH₂OH)-NH₂) | (structure: -C(=O)-NH-CH(CH₂OH)-(3-Cl,4-F-phenyl)) |
| II-16 | Cl | (structure: -NH-C(=O)-CH(CH₂CH₂S(=O)CH₃)-NH-C(=O)-CH₃) | (structure: -C(=O)-NH-CH(CH₂OH)-(3-Cl,4-F-phenyl)) |

TABLE 1-continued

Compounds II-A, II-B, and II-C

| No. | R² | —L—A | Qₙ—R⁴ |
|---|---|---|---|
| II-17 | Cl | (structure: -CH2-NH-C(O)-CH(CH2OH)-NH-C(O)O-C(CH3)3) | (structure: -C(O)-NH-CH(CH2OH)-(3-Cl,4-F-phenyl)) |
| II-18 | Cl | (structure: -CH2-NH-C(O)-CH(CH2OH)-NH2) | (structure: -C(O)-NH-CH(CH2OH)-(3-Cl,4-F-phenyl)) |
| II-19 | Cl | (structure: -CH2-NH-C(O)-CH(CH2OH)-NH-C(O)CH3) | (structure: -C(O)-NH-CH(CH2OH)-(3-Cl-phenyl)) |
| II-20 | Cl | (structure: -CH2-NH-C(O)-CH(CH2OH)-NH-C(O)CH3) | (structure: -C(O)-NH-CH(CH2OH)-(3-Cl,4-F-phenyl)) |
| II-21 | Cl | (structure: -CH2-NH-C(O)-CH(CH(CH3)2)-NH-C(O)CH3) | (structure: -C(O)-NH-CH(CH2OH)-(3-Cl,4-F-phenyl)) |
| II-22 | Cl | (structure: -CH2-NH-CH2CH2CH2CH3) | (structure: -C(O)-NH-CH(CH2OH)-(3-Cl,4-F-phenyl)) |
| II-23 | Cl | (structure: -CH2-N(C4H9)(C4H9)) | (structure: -C(O)-NH-CH(CH2OH)-(3-Cl,4-F-phenyl)) |
| II-24 | Cl | (structure: -CH2-NH-C(O)-CH(CH2OH)-NH-C(O)CH3) | (structure: -C(O)-NH-CH(CH2OH)-(3-Cl,4-F-phenyl)) |

TABLE 1-continued

Compounds II-A, II-B, and II-C

| No. | R² | —L—A | Qₙ—R⁴ |
|---|---|---|---|
| II-25 | Cl | ⸺NH-C(=O)-CH(CH₂OH)-NH-C(=O)-CH₃ | ⸺C(=O)-NH-CH(CH₂OH)-(3-Cl,4-F-phenyl) |
| II-26 | Cl | ⸺NH-CH₂CH₃ (ethylamino) | ⸺C(=O)-NH-CH(CH₂OH)-(3-Cl,4-F-phenyl) |
| II-27 | Cl | ⸺NH-CH₂CH₂CH₃ (propylamino) | ⸺C(=O)-NH-CH(CH₂OH)-(3-Cl,4-F-phenyl) |
| II-28 | Cl | ⸺N(CH₂CH₂CH₃)₂ (dipropylamino) | ⸺C(=O)-NH-CH(CH₂OH)-(3-Cl,4-F-phenyl) |
| II-29 | Cl | ⸺NH-CH₂-C(=O)-OEt | ⸺C(=O)-NH-CH(CH₂OH)-(3-Cl,4-F-phenyl) |
| II-30 | Cl | ⸺NH-CH₂CH₂-OH | ⸺C(=O)-NH-CH(CH₂OH)-(3-Cl,4-F-phenyl) |
| II-31 | Cl | ⸺NH-CH₂-CH(OH)-CH₃ | ⸺C(=O)-NH-CH(CH₂OH)-(3-Cl,4-F-phenyl) |
| II-32 | Cl | ⸺NH-CH₂CH₂-CH(OH)-CH₃ | ⸺C(=O)-NH-CH(CH₂OH)-(3-Cl,4-F-phenyl) |

TABLE 1-continued

Compounds II-A, II-B, and II-C

| No. | R² | —L—A | Qₙ—R⁴ |
|---|---|---|---|
| II-33 | Cl | ~CH2-NH-CH2-C≡N | ~C(O)-NH-CH(CH2OH)-(3-Cl,4-F-phenyl) |
| II-34 | Cl | ~CH2-N(CH2CH3)2 | ~C(O)-NH-CH(CH2OH)-(3-Cl,4-F-phenyl) |
| II-35 | Cl | ~CH2-NH-CH2CH2-Cl | ~C(O)-NH-CH(CH2OH)-(3-Cl,4-F-phenyl) |
| II-36 | Cl | ~CH2-N(CH2CH2Cl)2 | ~C(O)-NH-CH(CH2OH)-(3-Cl,4-F-phenyl) |
| II-37 | Cl | ~CH2-NH-CH2CH2-NH-C(O)-O-C(CH3)3 | ~C(O)-NH-CH(CH2OH)-(3-Cl,4-F-phenyl) |
| II-38 | Cl | ~CH2-NH-C(O)-CH2-N(CH2CH3)2 | ~C(O)-NH-CH(CH2OH)-(3-Cl,4-F-phenyl) |
| II-39 | Cl | * ~CH2-NH-C(O)-NH-(CH2)3CH3 | ~C(O)-NH-CH(CH2OH)-phenyl |
| II-40 | Cl | * ~CH2-NH-C(O)-NH-(CH2)3CH3 | ~C(O)-NH-CH(phenyl)-CH2-O-C(O)-NH-(CH2)2CH3 |

TABLE 1-continued
Compounds II-A, II-B, and II-C
| No. | R² | —L—A | Qₙ—R⁴ |
|---|---|---|---|
| II-41 | Cl | 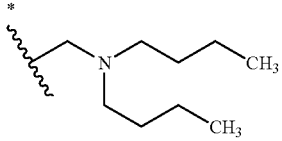 | 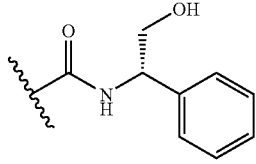 |
| II-42 | Cl | 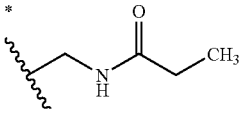 | 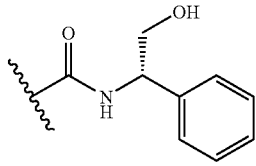 |
| II-43 | Cl | 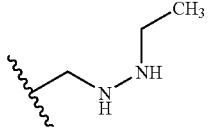 | 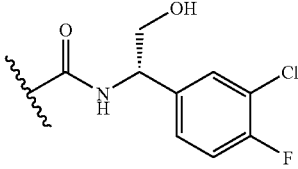 |
| II-44 | Cl | 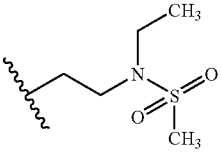 | 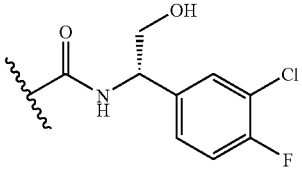 |
| II-45 | 3,5-Cl | 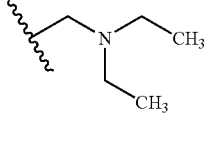 | 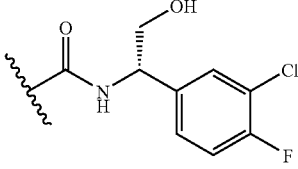 |
| II-46 | Cl | 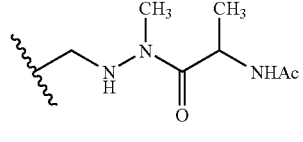 | 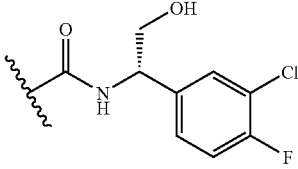 |
| II-47 | Cl | 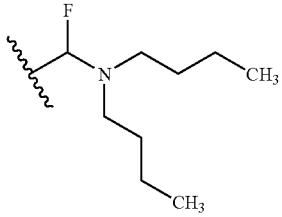 | 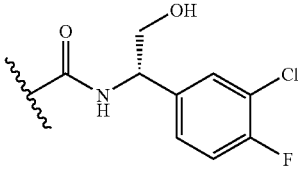 |
| II-48 | 3-F-5-CF₃ | 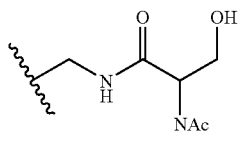 | 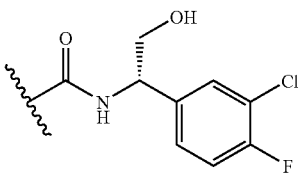 |

TABLE 1-continued

Compounds II-A, II-B, and II-C

| No. | R² | —L—A | Qₙ—R⁴ |
|---|---|---|---|
| II-49 | Cl | [structure: -CH₂CH₂-O-CH₂CH₂-N(CH₃)₂] | [structure: -C(=O)-NH-CH(CH₂OH)-(3-Cl,4-F-phenyl)] |
| II-50 | Cl | [structure: -CH(Me)-NH-CH₂-C(=O)-N(CH₃)₂] | [structure: -C(=O)-NH-CH(CH₂OH)-(3-Cl,4-F-phenyl)] |
| II-51 | 3-F-<br>5-CF₃ | [structure: -NH-C(=O)-CH(NAc)-CH₂OH] | [structure: -C(=O)-NH-CH(CH₂OH)-(3-Cl,4-F-phenyl)] |

\* = —L—A is at the 5-position

Additional exemplary structures of formula II-A, II-B, and II-C wherein the phenyl ring is substituted with one R² at the 3-position, R¹ is H, R³ is H, n is one, and -L-A is at the 4-position are set forth in Table 2 below.

TABLE 2

Additional Compounds of Formulae II-A, II-B, and II-C

| No. | R² | —L—A | Qₙ—R⁴ |
|---|---|---|---|
| II-52 | Cl | [structure: -CH₂CH₂-NH-CH(CH₃)-CH₂-C(=O)-N(CH₃)₂] | [structure: -C(=O)-NH-CH(CH₂OH)-(3-Cl,4-F-phenyl)] |
| II-53 | Cl | [structure: -CH₂-NH-CH₂-C(=O)-CH₂CH₃] | [structure: -C(=O)-NH-CH(CH₂OH)-(3-Cl,4-F-phenyl)] |
| II-54 | Cl | [structure: -CH₂-N(CH(CH₃)₂)(CH₃)] | [structure: -C(=O)-NH-CH(CH₂OH)-(3-Cl,4-F-phenyl)] |

TABLE 2-continued

Additional Compounds of Formulae II-A, II-B, and II-C

| No. | R² | —L—A | Qₙ—R⁴ |
|---|---|---|---|
| II-55 | Cl | (ethyl alaninate linked via NH) | (amide-NH-CH(CH₂OH)-3-Cl-4-F-phenyl) |
| II-56 | Cl | (serinamide: NH-C(=O)-CH(NH₂)-CH₂OH) | (amide-NH-CH(CH₂OH)-3-Cl-4-F-phenyl) |
| II-57 | CF₃ | (NH-CH(CH₃)₂, isopropylamino) | (amide-NH-CH(CH₂OH)-3-Cl-4-F-phenyl) |
| II-58 | CF₃ | (N(CH₃)-CH(CH₃)-COOH) | (amide-NH-CH(CH₂OH)-3-Cl-4-F-phenyl) |
| II-59 | CF₃ | (N(CH₃)-CH(CH₃)-C(=O)-NHCH₃) | (amide-NH-CH(CH₂OH)-3-Cl-4-F-phenyl) |
| II-60 | CF₃ | (NH-CH(CH₃)-C(=O)-N(CH₃)₂) | (amide-NH-CH(CH₂OH)-3-Cl-4-F-phenyl) |
| II-61 | CF₃ | (N(CH₃)-CH(CH₃)-C(=O)-N(CH₃)₂) | (amide-NH-CH(CH₂OH)-3-Cl-4-F-phenyl) |
| II-62 | CF₃ | (ethyl alaninate: NH-CH(CH₃)-C(=O)-O-CH₂CH₃) | (amide-NH-CH(CH₂OH)-3-Cl-4-F-phenyl) |

TABLE 2-continued

Additional Compounds of Formulae II-A, II-B, and II-C

| No. | R² | —L—A | Qₙ—R⁴ |
|---|---|---|---|
| II-63 | Cl | [structure: N(CH₃)-CH(CH₃)-C(=O)-O-CH₂CH₃] | [structure: C(=O)-NH-CH(CH₂OH)-(3-Cl,4-F-phenyl)] |
| II-64 | CF₃ | [structure: N(CH₃)-CH(CH₃)-C(=O)-O-CH₂CH₃] | [structure: C(=O)-NH-CH(CH₂OH)-(3-Cl,4-F-phenyl)] |
| II-65 | CF₃ | [structure: NH-CH(CH₃)-C(=O)-NH-CH₃] | [structure: C(=O)-NH-CH(CH₂OH)-(3-Cl,4-F-phenyl)] |
| II-66 | Cl | [structure: NH-CH(CH₃)-C(=O)-N(CH₃)₂] | [structure: C(=O)-NH-CH(CH₂OH)-(3-Cl,4-F-phenyl)] |
| II-67 | Cl | [structure: NH-C(=O)-CH(NHCH₃)-CH₂OH] | [structure: C(=O)-NH-CH(CH₂OH)-(3-Cl,4-F-phenyl)] |
| II-68 | Cl | [structure: NH-CH₂CH₂-NH₂] | [structure: C(=O)-NH-CH(CH₂OH)-(3-Cl,4-F-phenyl)] |
| II-69 | Cl | [structure: NH-C(=O)-CH(NH₂)-CH₃] | [structure: C(=O)-NH-CH(CH₂OH)-(3-Cl,4-F-phenyl)] |
| II-70 | Cl | [structure: NH-CH(CH₃)₂] | [structure: C(=O)-NH-CH(CH₂OH)-(3-Cl,4-F-phenyl)] |

TABLE 2-continued

Additional Compounds of Formulae II-A, II-B, and II-C

| No. | $R^2$ | —L—A | $Q_n$—$R^4$ |
|---|---|---|---|
| II-71 | Cl | (structure: –CH2–NH–CH2–C(=O)–NH–CH2–CH3) | (structure: –C(=O)–NH–CH(CH2OH)–(3-Cl,4-F-phenyl)) |
| II-72 | Cl | (structure: –CH2–NH–CH(CH3)–CH2–C(=O)–O–CH2–CH3) | (structure: –C(=O)–NH–CH(CH2OH)–(3-Cl,4-F-phenyl)) |
| II-73 | Cl | (structure: –CH2–N(CH2–C(=O)–CH2–CH3)2) | (structure: –C(=O)–NH–CH(CH2OH)–(3-Cl,4-F-phenyl)) |
| II-74 | Cl | (structure: –CH2–N(CH2–C(=O)–NH2)2) | (structure: –C(=O)–NH–CH(CH2OH)–(3-Cl,4-F-phenyl)) |
| II-75 | Cl | (structure: –CH2–NH–C(=O)–CH(NH2)–CH2–OH) | (structure: –C(=O)–NH–CH(CH2OH)–(3-Cl,4-F-phenyl)) |
| II-76 | Cl | (structure: –CH2–NH–CH2–C(=O)–NH2) | (structure: –C(=O)–NH–CH(CH2OH)–(3-Cl,4-F-phenyl)) |
| II-77 | Cl | (structure: –CH2–NH–C(=O)–CH(NH2)–CH(OH)–CH3) | (structure: –C(=O)–NH–CH(CH2OH)–(3-Cl,4-F-phenyl)) |
| II-78 | Cl | (structure: –CH2–NH–C(=O)–O–CH2–CH3) | (structure: –C(=O)–NH–CH(CH2OH)–(3-Cl,4-F-phenyl)) |

TABLE 2-continued

Additional Compounds of Formulae II-A, II-B, and II-C

| No. | R² | —L—A | Qₙ—R⁴ |
|---|---|---|---|
| II-79 | Cl | | |
| II-80 | Cl | | |
| II-81 | Cl | | |
| II-82 | Cl | | |
| II-83 | Cl | | |
| II-84 | Cl | | |
| II-85 | Cl | | |

TABLE 2-continued
Additional Compounds of Formulae II-A, II-B, and II-C
| No. | R² | —L—A | Qₙ—R⁴ |
|---|---|---|---|
| II-86 | Cl | 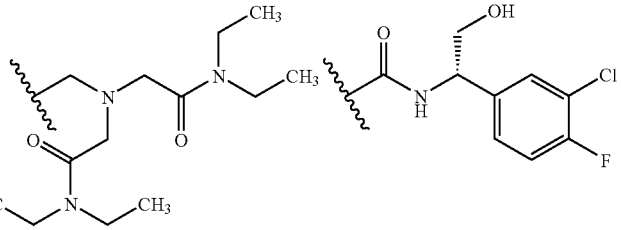 | |
Additional exemplary structures of formula I are set forth in Table 3 below.
TABLE 3
Additional compounds of formula I
| No. | Compound |
|---|---|
| I-1 | 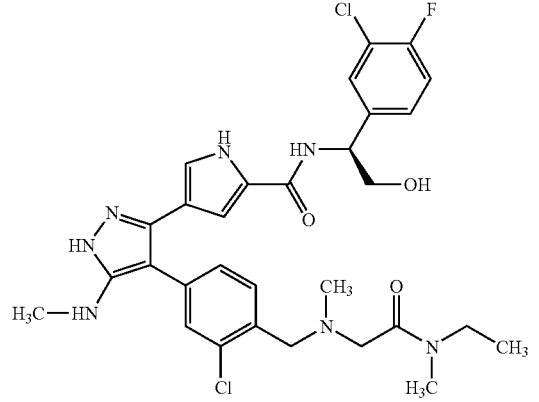 |
| I-2 | 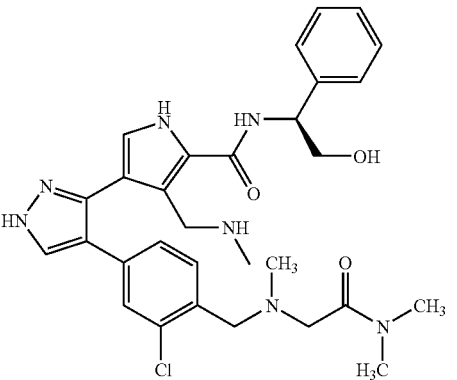 |
| I-3 | 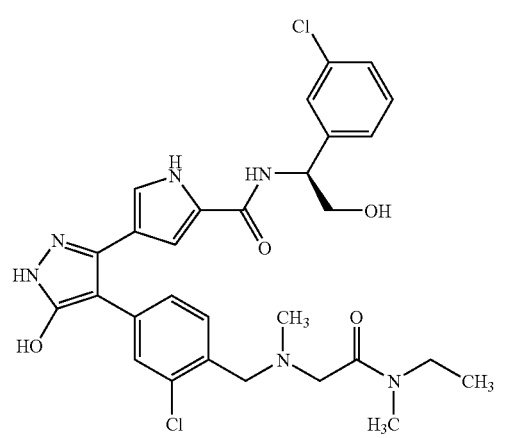 |
| I-4 | 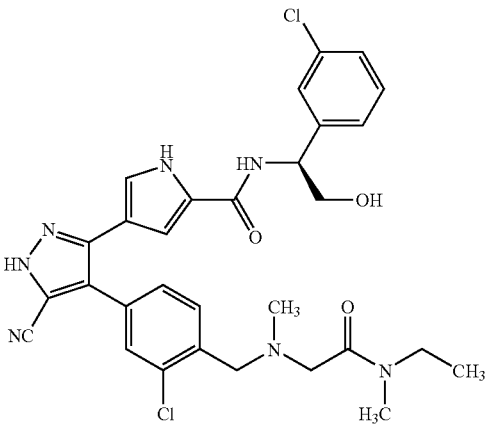 |

TABLE 3-continued

Additional compounds of formula I

| No. | Compound |
|-----|----------|
| I-5 | 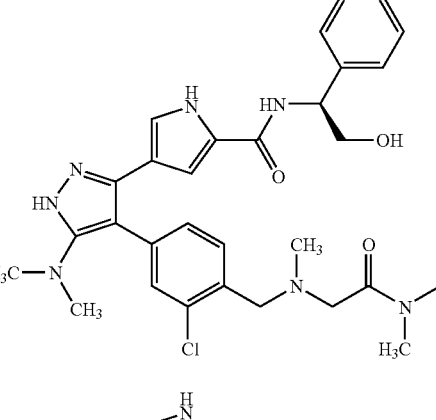 |
| I-6 | 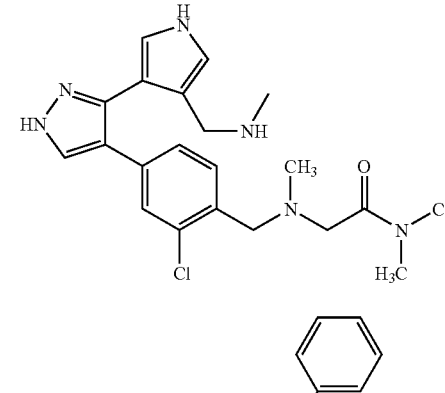 |
| I-7 | 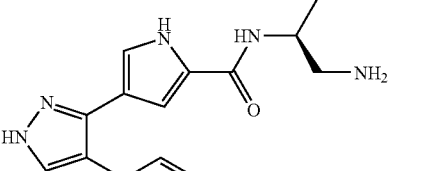 |

Another object of the invention is to provide methods of producing the above-identified compounds of formula I. The present compounds may be prepared in general by methods known to those skilled in the art for analogous compounds, as illustrated by the general Schemes I and II and the synthetic examples shown below.

Scheme I

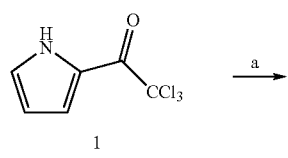

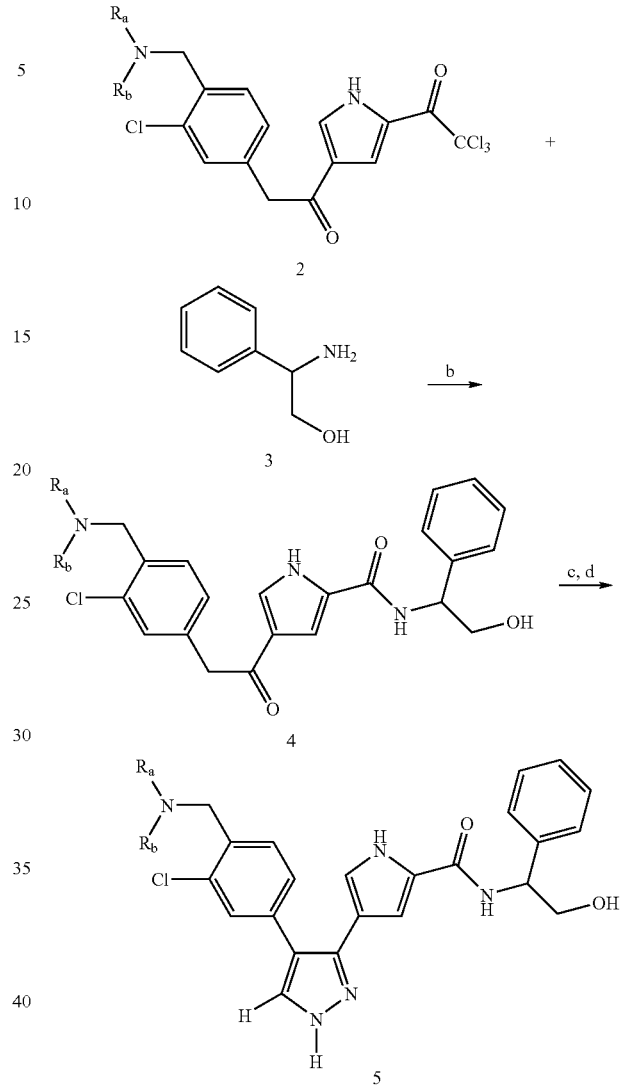

Reagents and conditions: (a) 3-Cl-4- ($R_a$) ($R_b$) aminomethyl-PhCH$_2$COCl, AlCl$_3$, CH$_2$Cl$_2$, 2 hours, RT; (b) DMF, 24 hrs, room temperature; (c) (Me$_2$N)$_2$—COt-Bu, THF, 24 hrs, room temperature; and (d) H$_2$NHNH$_2$, EtOH, 12 hours, reflux Scheme I above shows a general synthetic route that was used for preparing the compounds of this invention. In step (a), a substituted benzoyl chloride was combined with compound 1 in dichloromethane and aluminum trichloride to form compound 2. A wide variety of benzylamine derivatives are amenable to this reaction, including compounds wherein $R_a$ and $R_b$ are independently selected from the group consisting of $R^8$ and A as described above.

The formation of amide 4 was achieved by treating compound 2 with an amine 3 in DMF. When amine 3 was a primary amine, the reaction proceeded at ambient temperature. When amine 3 was a secondary amine, the reaction was heated at 50° C. to achieve complete reaction and afford amide 4.

The formation of enamine at step (c) was achieved by treating amide 4 with (Me$_2$N)$_2$—COt-Bu at ambient temperature. Alternatively, the reaction to form the enamine at step (c) was also achieved by using dimethylformamide-dimethylacetal (DMF-DMA). The reaction using DMF- DMA requires elevated temperature to afford enamine whereas using (Me₂N)₂—COtBu has the advantage of proceeding at ambient temperature to afford the enamine in higher purity.

The formation of the pyrazole compound 5 at step (d) was achieved by the treatment of the enamine with hydrazine hydrate in ethanol at elevated temperature. The compounds of formula II synthesized by this method, as exemplified in Table 1, were isolated by preparatory HPLC (reverse phase, 10→90% MeCN in water over 15 minutes). The details of the conditions used for producing these compounds are set forth in the Examples.

Scheme II

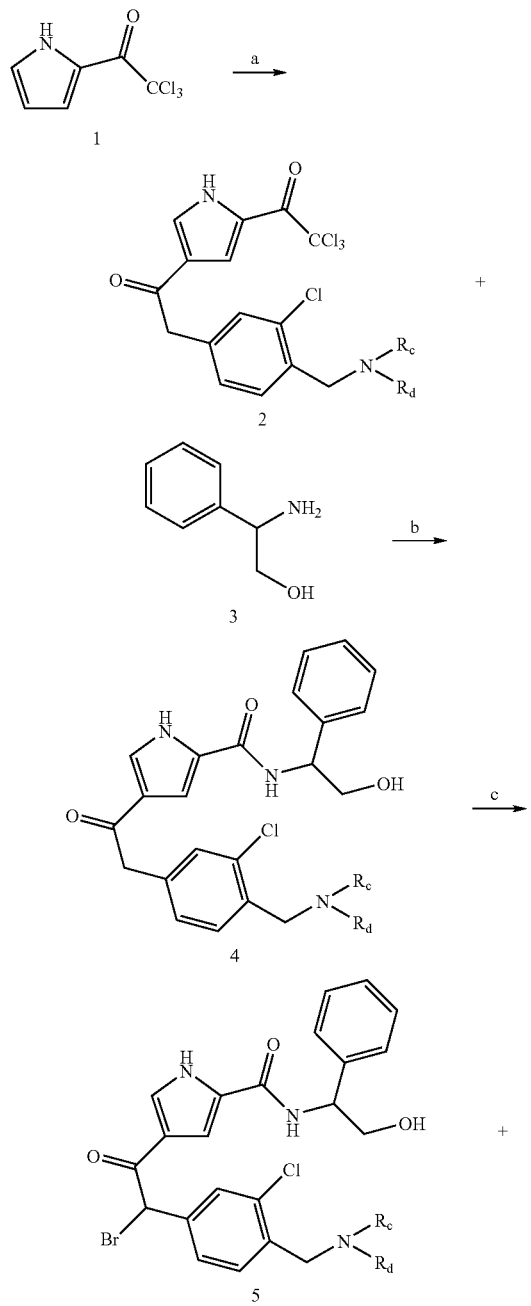

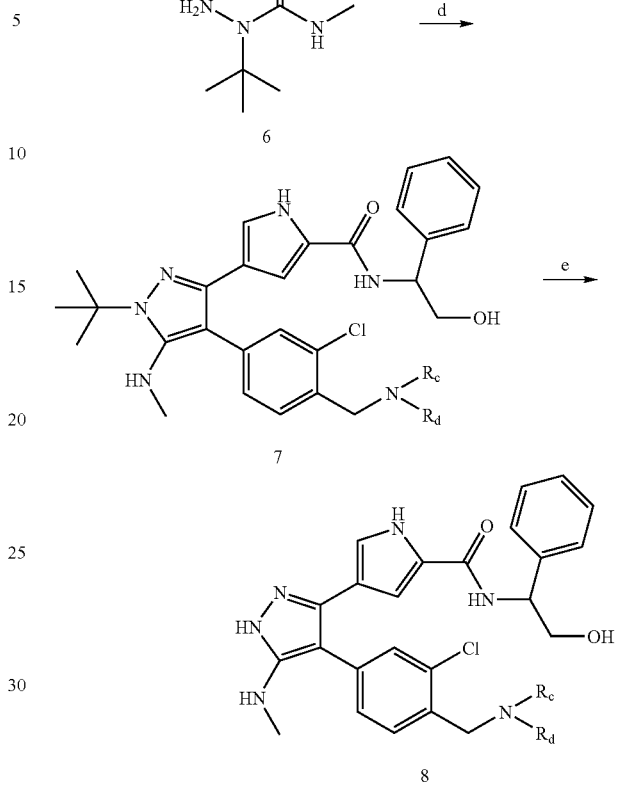

Reagents and conditions: (a) 3-Cl-4- ($R_c$) ($R_d$) aminomethyl-PhCH₂COCl, AlCl₃, CH₂Cl₂, 2 hours, RT; (b) DMF, 24 hrs, room temperature; (c) NBS, CCl₄ reflux; (d) iPrOH, reflux; and (e) formic acid, reflux, 2 hours.

Scheme II above shows a general synthetic method that may be used for preparing compounds wherein $R^1$ is $NHR^7$. A wide variety of benzylamine derivatives are amenable to this reaction, including compounds wherein $R_c$ and $R_d$ are independently selected from the group consisting of $R^8$ and A as described above. This method is modified from that of Jira, T., et al., *Pharmazie*, pp. 401–406 (1994). These compounds of may also be prepared by methods similar to those of Woller, J., et al, *Pharmazie*, pp. 937–940 (1996), Rychmans, T., et al, *Tetrahedron*, pp. 1729–1734 (1997), and Tupper, D. E., et al, *Synthesis*, pp. 337–341 (1997).

The activity of a compound utilized in this invention as an inhibitor of ERK or AKT, may be assayed in vitro, in vivo or in a cell line according to methods known in the art. In vitro assays include assays that determine inhibition of either the phosphorylation activity or ATPase activity of activated ERK or AKT. Alternate in vitro assays quantitate the ability of the inhibitor to bind to ERK or AKT. Inhibitor binding may be measured by radiolabelling the inhibitor prior to binding, isolating the inhibitor/ERK or inhibitor/AKT complex and determining the amount of radiolabel bound. Alternatively, inhibitor binding may be determined by running a competition experiment where new inhibitors are incubated with ERK or AKT bound to known radioligands. Detailed conditions for assaying a compound utilized in this invention as an inhibitor of ERK or AKT kinase are set forth in the Examples below.

According to another embodiment, the invention provides a composition comprising a compound of this invention or a pharmaceutically acceptable derivative thereof and a pharmaceutically acceptable carrier, adjuvant, or vehicle. The amount of the compound in the compositions of this invention is such that is effective to detectably inhibit a protein kinase, particularly ERK or AKT in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in ERK or AKT activity between a sample comprising said composition and an ERK or AKT kinase and an equivalent sample comprising ERK or AKT kinase in the absence of said composition. According to a preferred embodiment, inhibition of kinase activity by a compound according to the present invention is greater than 10% compared to the kinase activity in the absence of the compound. Preferably, inhibition is greater than 20%, 30%, or 40%, and even more preferably greater than 50%, 60%, 70%, 80%, or 90%.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+$ ($C_{1-4}$ alkyl)$_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, and the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the compounds of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the invention relates to a method of inhibiting ERK or AKT kinase activity in a biological sample comprising the step of contacting said biological sample with a compound of this invention, or a pharmaceutically acceptable composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of ERK or AKT kinase activity in a biological sample is useful for a variety of purposes that are known to one of skill in the art. Examples of such purposes include, but are not limited to, blood transfusion, organ-transplantation, biological specimen storage, and biological assays.

According to another embodiment, the invention provides a method for treating or lessening the severity of an ERK-mediated disease or condition in a patient comprising the step of administering to said patient a pharmaceutically acceptable composition according to the present invention.

The term "ERK-mediated condition" or "disease", as used herein, means any disease or other deleterious condition in which ERK is known to play a role. The term "ERK-mediated condition" or "disease" also means those diseases or conditions that are alleviated by treatment with an ERK inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

According to another embodiment, the invention provides a method for treating or lessening the severity of an AKT-mediated disease or condition in a patient comprising the step of administering to said patient a pharmaceutically acceptable composition according to the present invention.

The term "AKT-mediated condition" or "disease", as used herein, means any disease state or other deleterious condition in which AKT is known to play a role. AKT-mediated diseases or conditions include, but are not limited to, proliferative disorders, cancer, and neurodegenerative disorders.

Compounds of the present invention are also useful as inhibitors of related kinases to ERK. The term "related kinases" refer to protein kinases having residues which are similar to those residues which line the ERK binding site. Without wishing to be bound by theory, applicants speculate that this inhibitory activity is due to the close structural similarity between the active sites of ERK and related kinases. The alignment of the ERK sequence with other kinases can be derived from common software programs such as the "bestfit" program available from Genetics Computer Group. This program uses the local homology algorithm described by Smith and Waterman in *Advances in Applied Mathematics* 2; 482 (1981).

Related kinases inhibited by the compounds of this invention would contain residues, identified by the above standard protein sequence alignment software, corresponding to the ERK residues: I31, E33, G34, A35, Y36, G37, M38, V39, A52, K54, R67, T68, E71, L75, I84, I86, I103, Q105, D106, L107, M108, E109, Dill, K114, D149, K151, S153, N154, L156, C166, and D167, with a similarity score of 80% or greater. In a more preferred embodiment the similarity score is 85%, more preferably 90%, even more preferably 95%, 96%, 97% or 98%. The similarity score may be determined using standard amino acid substitution tables such as those described by Dayhoff (Dayhoff, M. O., et al, *Atlas of Protein Sequence and Structure,* 1979) and Blosom-Henikoff (Blosum-Henikoff, S and Henikoff, J. G., *PNAS,* 1992,89:10915–10919). The term "related kinases" also includes those containing residues with a similarity score of 80% or greater to the following ERK residues: I31, G37, A52, I103, E109, and N154. In a more preferred embodiment the similarity score is 85%, more preferably 90%, even more preferably 95%, 96%, 97% or 98%.

The present method is especially useful for treating a disease that is alleviated by the use of an inhibitor of ERK or related kinases. As used herein, unless otherwise indicated, the term "ERK" refers to all isoforms of the ERK enzyme including, but not limited to, ERK1, ERK2, ERK3, ERK4, ERK5, ERK6, and ERK7.

In an alternate embodiment, the methods of this invention that utilize compositions that do not contain an additional therapeutic agent, comprise the additional step of separately administering to said patient an additional therapeutic agent. When these additional therapeutic agents are administered separately, they may be administered to the patient prior to, sequentially with or following administration of the compositions of this invention.

The compounds of this invention or pharmaceutically acceptable compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121, the contents of which are incorporated by reference herein in their entirety. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may be further covered by thereof to impart controlled release characteristics in the composition. Implantable devices coated with a compound of this invention are another embodiment of the present invention.

In order that the invention described herein may be more fully understood the following examples are set forth. It should be understood that these examples are for illustrative purposes only and are not to be construed as limiting this invention in any manner.

EXAMPLES

Example 1

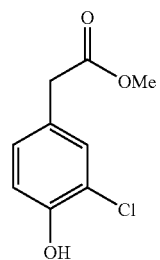

3

(3-Chloro-4-hydroxy-phenyl)-acetic acid methyl ester (3)

To a solution of 3-chloro-4-hydroxyphenyl acetic acid (20 mmol) in methanol (50 mL) was added concentrated HCl solution (5 mL), and stirred for 1 h at 50° C. After excess solvents were removed under vacuum, the residue was dissolved in EtOAc (50 mL) and washed with sat. NaHCO$_3$ solution (2×30 mL), brine (30 mL) and dried over anhydrous Na$_2$SO$_4$. This afforded methyl 3-chloro-4-hydroxy acetate 3 as a colorless oil (4.0 g, 99%). $^1$H NMR (CDCl$_3$) 6.9–7.0 (d, 1H), 6.8–6.9 (d, 1H), 5.4 (s, 1H), 3.6 (s, 3H), 3.4 (s, 2H).

Example 2

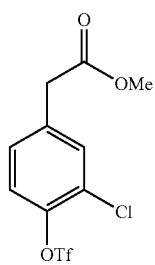

(3-Chloro-4-trifluoromethanesulfonyloxy-phenyl)-acetic acid methyl ester (4)

To the methyl ester 3 (4.0 g, 20 mmol) in CH$_2$Cl$_2$ (40 mL) was added TEA (2.8 mL, 20 mmol) and triflic anhydride (3.4 mL, 20 mmol) at 0° C. and stirred for 1 h. The reaction mixture was poured into a solution of saturated NaHCO$_3$ (40 mL) and extracted with EtOAc (3×30 mL). The organic extract was washed with brine and dried over anhydrous MgSO$_4$. After the organic solvents were removed in vacuo, this gave triflate 4 as a brown oil (6.0 g, 18 mmol). HPLC showed a single peak at 12.5 min. $^1$HNMR (CDCl$_3$) 7.5 (s, 1H), 7.2 (m, 1H), 7.1 (m, 1H), 3.7 (s, 3H), 3.6 (s, 2H).

Example 3

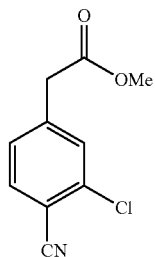

(3-Chloro-4-cyano)-acetic acid methyl ester (5)

To a solution of the triflate 4 (6.0 g, 18 mmol) in DMF (10 mL) was added zinc cyanide (2.13 g, 18.2 mmol) and tetrakis(triphenylphosphine) palladium(0) (2.1 g, 1.8 mmol). The resulting mixture was stirred for 15 h at 80° C. and then cooled to room temperature, diluted with EtOAC (50 mL) and poured into a saturated NaHCO$_3$ solution (30 mL). A white precipitate was removed by vacuum filtration. The filtrate was washed with H$_2$O, dried over anhydrous Na$_2$SO$_4$ and concentrated in vacuo. The crude products were purified from Silica Gel chromatography with 20% EtOAc/hexane. This gave methyl 3-chloro-4-cyanophenyl acetate 5 as a white solid (2.7 g, 72%). HPLC showed a single peak at 8.69 min. $^1$H NMR (CDCl$_3$) 7.7 (d, 1H), 7.5 (s, 1H), 7.3 (d, 1H), 3.7 (s, 3H), 3.6 (s, 2H).

Example 4

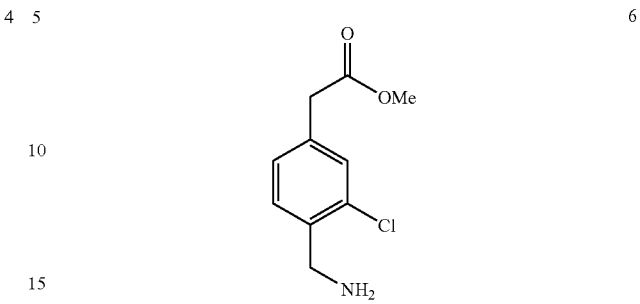

(4-Aminomethyl-3-chloro)-acetic acid methyl ester (6)

A solution of methyl 3-chloro-4-cyanophenyl acetate 5 (2.7 g, 13 mmol) in 1M of NH$_3$/CH$_3$OH (120 mL) was added Raney Nickle (200 mg). The mixture was shaken for 20 h under 30–40 psi H$_2$. The catalyst was removed by filtration through a layer of celite. The filtrate was concentrated under vacuum. The residue was dissolved in EtOAc (100 mL), washed with brine (70 mL), dried over anhydrous Na$_2$SO$_4$ and concentrated in vacuo. This afforded a green oil 6 (2.3 g, 85%). HPLC gave a single peak at 3.68 min. The product was carried over to next step without purification.

Example 5

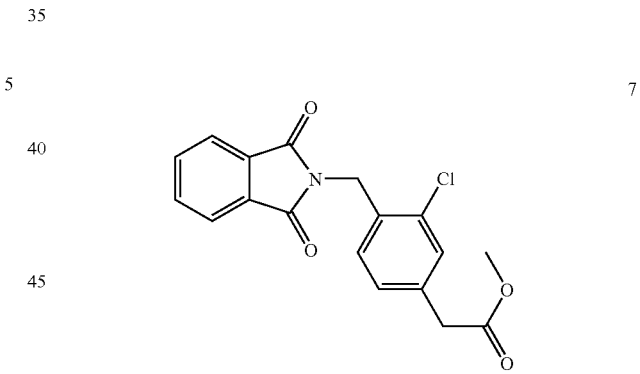

[3-Chloro-4-(1,3-dihydro-isoindol-2-ylmethyl-phenyl]-acetic acid methyl ester (7)

To a solution of the benzyl amine 6 (2.1 g, 10 mmol) in toluene (100 mL) was added phthalic anhydride (1.62 g, 11 mmol), then stirred for 1 h at 50° C. To the mixture was added ZnBr$_2$ (2.25 g, 10 mmol) and HMDS (2.3 g, 14.2 mmol). The mixture was stirred for 4 h at 50–60° C. The reaction mixture was cooled to room temperature, then poured into 0.5 M HCl solution and extracted with EtOAc. The organic layers were combined, concentrated and afforded slightly yellow solids. The crude products were purified from flash column with 30% EtOAC/hexanes. This gave 2.8 g of compound 7 as white solid. $^1$HNMR (CDCl$_3$) 7.8–7.9 (d, 2H), 7.7–7.8 (d, 2H), 7.3 (s, 1H), 7.2 (d, 1H), 5.0 (s, 2H), 3.7 (s, 3H), 3.6 (s, 2H), H), 7.1 (d, 1H).

Example 6

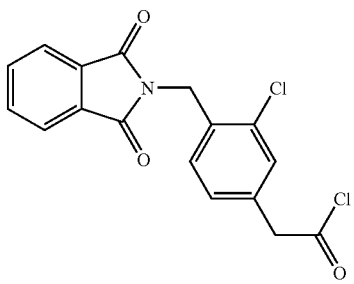

[3-Chloro-4-(1,3-dihydro-isoindol-2-ylmethyl-phenyl]-acetyl chloride (9)

To a solution of methyl ester 7 (2.2 g, 6.4 mmol) in methanol (60 mL) was added 1M of NaOH (20 mL). The resulting solution was stirred for 1 h at room temperature. The solvents were removed under vacuum. The residues were neutralized with 1 M HCl solution to pH 3. The white precipitate was collected by vacuum filtration, washed with $H_2O$, diethyl ether and then dried under vacuum. This afforded acid 8 as a white solid. The acid 8 (1.4 g, 4 mmol) was suspended in toluene (50 mL). To the suspension was added thionyl chloride (0.8 mL, 10.8 mmol) and a few drops of DMF. The mixture was stirred overnight at room temperature and the solvents removed under vacuum to afford acid chloride 9. $^1$HNMR (CDCl$_3$) 7.8–7.9 (m, 2H), 7.7–7.8 (m, 2H), 7.2 (s, 1H), 7.1 (d, 1H), 7.0 (d, 1H), 4.9 (s, 2H), 4.0 (s, 2H).

Example 7

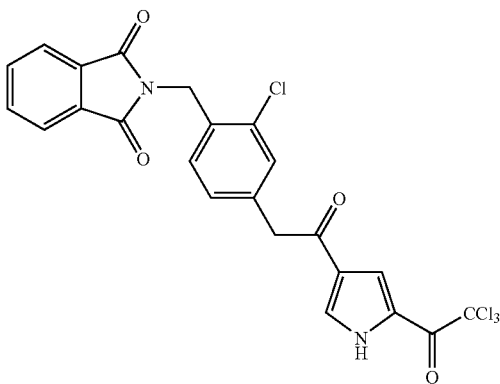

2-(2-Chloro-4-{2-oxo-2-[5-(2,2,2-trichloro-acetyl)-1H-pyrrol-3-yl-]-ethyl}-benzyl)-isoindole-1,3-dione (10)

To the acid chloride 9 (2.0 g, 4 mmol) in CH$_2$Cl$_2$ (2 mL) was added trichloroacetyl pyrrole (860 mg, 4 mmol) and AlCl$_3$ (540 mg, 4 mmol). The resulting solution was stirred for 2 h at room temperature and then diluted with EtOAc (40 mL). The mixture was filtered through a layer of silica gel, then concentrated under vacuum. The crude products were purified from silica gel column with 50% EtOAc/hexanes. This gave 1.6 g of product 10 (78%). $^1$H NMR (CDCl$_3$) 9.9 (br, 1H), 8.1 (m, 2H), 8.0 (m, 2H), 7.9 (s, 1H), 7.8 (d, 1H), 7.5 (s, 1H), 7.4 (d, 1H), 7.3 (dd, 1H), 5.2 (s, 2H), 4.3 (s, 2H).

Example 8

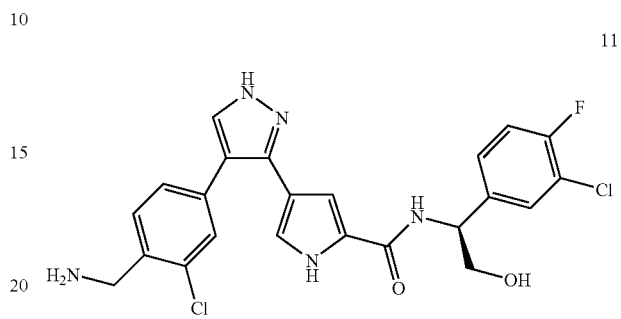

4-[4-(4-Aminomethyl-3-chloro-phenyl)-1H-pyrazol-3-yl]-1H-pyrrole-2-carboxylic acid [1-(3-chloro-4-fluoro-phenyl)-2-hydroxy-ethyl]-amide (11)

To a solution of compound 10 (1.0 mmol) in DMF (5 mL) was added (S) 3-chloro-4-fluoro phenyl glycinol (1.2 mmol), then stirred for 15 h. The solvent was concentrated under vacuum. To the residue (1.0 mmol) in THF (1 mL) was added tert-butyl bis(dimethylamino)-methane (1 mL, 5 mmol). The mixture was stirred for 15 h at 50° C. and then concentrated under vacuum. To the residue (1 mmol) was added C$_2$H$_5$OH (5 mL) and hydrazine hydrate (1 mL, 20 mmol). The mixture was refluxed for 3 h and cooled to room temperature. The solvents were removed under vacuum and the crude products were purified from preparatory HPLC. This afforded the product 11 as a white solid. $^1$HNMR (CD$_3$OD) 7.6 (s, 1H), 7.4 (s, 1H), 7.2–7.4 (m, 3H), 7.1–7.2 (m, 1H), 7.0 (t, 1H), 6.8 (d, 2H), 4.9 (t, 1H), 4.1 (s, 2H), 3.6 (dd, 2H).

Example 9

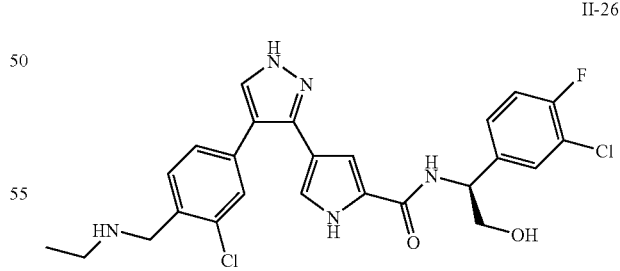

II-26

4-[4-(3-Chloro-4-ethylaminomethyl-phenyl)-1H-pyrazol-3-yl]-1H-pyrrole-2-carboxylic acid [1-(3-chloro-4-fluoro-phenyl)-2-hydroxy-ethyl]-amide (II-26)

To the benzyl amine 11 (0.1 mmol) in CH$_3$OH (1.0 mL) was added 4 Å molecular seives (10 mg), acetaldehyde (0.1 mmol) and Py-BH₃ (0.1 mmol) at 0° C. The mixture was stirred for 2 h at 0+ C. and then 6 h at room temperature. The reaction was quenched with 4 M HCl solution (0.5 mL). The crude product was purified from preparatory HPLC to give secondary amine II-26 as a white solid. ¹H NMR (CD₃OD) 7.8 (s, 1H), 7.5 (s, 1H), 7.4–7.5 (m, 3H), 7.2–7.3 (m, 1H), 7.1–7.2 (m, 1H), 6.9 (d, 2H), 5.1 (m, 1H), 4.3 (s, 2H), 3.6–3.7 (m, 2H), 3.1 (t, 2H), 1.3 (t, 3H).

Example 10

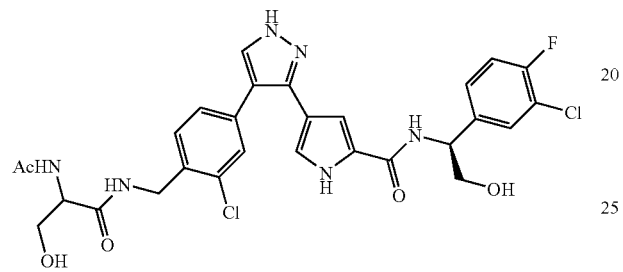

4-(4-{4-[(2-Acetylamino-3-hydroxy-propionylamino)-methyl]-3-chloro-phenyl}-1H-pyrazol-3-yl)-1H-pyrrole-2-carboxylic acid [1-(3-chloro-4-fluoro-phenyl)-2-hydroxyethyl]-amide (II-20)

To a solution of N—Ac-Ser-OH (0.2 mmol) in DMF (5 mL) was added HOBt (0.4 mmol) and EDCI (0.22 mmol) and stirred for 5 min. To the solution was added benzyl amine 11 (0.2 mmol) and TEA (0.3 mmol). The reaction mixture was stirred for 2 h at room temperature. The crude products were purified from preparatory HPLC to afford the desired product II-20 as a white solid. ¹HNMR (CD₃OD) 8.5 (br, 1H), 7.6 (s, 1H), 7.5 (m, 1H), 7.4 (s, 1H), 7.2–7.3 (m, 3H), 7.1 (t, 1H), 6.8–6.9 (m, 2H), 5.0 (t, 1H), 4.2–4.4 (m, 3H), 3.6–3.7 (m, 4H), 1.9 (s, 3H).

Example 11

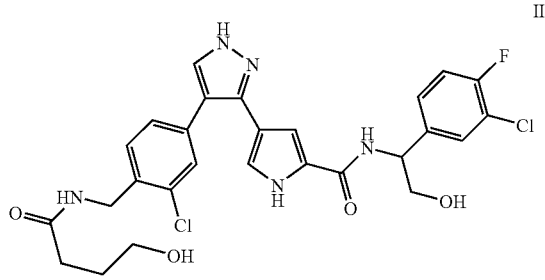

4-(4-{3-Chloro-4-[(4-hydroxy-butyrylamino)-methyl]-phenyl}-1H-pyrazol-3-yl)-1H-pyrrole-2-carboxylic acid [1-(3-chloro-4-fluoro-phenyl)-2-hydroxy-ethyl]-amide (II-8)

A solution of benzyl amine 11 (0.05 mmol) in DMSO (1 mL) was mixed with a solution of 4-butyrolactone (0.05 mmol) in CH₂Cl₂ (1 mL) under N₂. To the mixture was added AlMe₃ (0.25 mmol) and stirred for 10 min at room temperature and then 6 h at 45° C. The crude product was purified from preparatory HPLC to give II-8 as a yellow oil.

Example 12

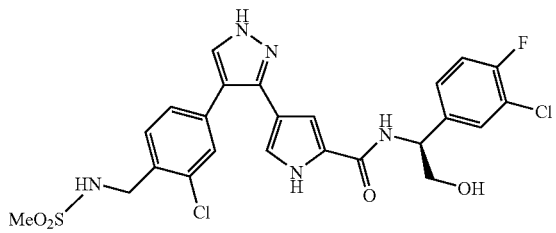

4-{4-[3-Chloro-4-(methanesulfonylamino-methyl)-phenyl]-1H-pyrazol-3-yl}-1H-pyrrole-2-carboxylic acid [1-(3-chloro-4-fluoro-phenyl)-2-hydroxy-ethyl]-amide (II-2)

To a solution of benzyl amine 11 (0.05 mmol) in DMF (3 mL) was added iPr₂NEt (0.1 mmol) and methane sulfonic anhydride (0.06 mmol). The resulting solution was stirred for 5 h at room temperature. The solvent was removed under vacuum and the crude products were purified from preparatory HPLC. This afforded II-2 as a yellow oil.

Example 13

We have prepared other compounds of formula II by methods substantially similar to those described in the above Examples 1–12 and those illustrated in Scheme I. The characterization data for these compounds is summarized in Table 4 below and includes LC/MS, HPLC, and ¹H NMR data.

For compounds where the HPLC Method is designated as "A", the following method was utilized: a gradient of water:MeCN, 0.1% TFA (95:5→0:100) was run over 22 minutes at 1 mL/min and 214 nm. For compounds where the HPLC Method is designated as "B", the following method was utilized: a gradient of water:MeCN, 0.1% TFA (90:10→0:100) was run over 8 minutes at 1 mL/min and 214 nm. Each of methods A and B utilizes the YMC ODS-AQ 55 120 A column with a size of 3.0×150 mm. The term "$T_{ret}$(min)" refers to the retention time, in minutes, associated with the compound using the designated HPLC method.

Where applicable, ¹H NMR data is also summarized in Table 4 below wherein "Y" designates ¹H NMR data is available and was found to be consistent with structure. Compound numbers correspond to the compound numbers listed in Tables 1–3.

TABLE 4

Characterization Data for Selected Compounds

| Compound No. | M + 1 | HPLC Method | $T_{ret}$ (min) | HPLC % | $^1$H NMR |
|---|---|---|---|---|---|
| II-1 | 556.2 | B | 7.55 | 100 | — |
| II-2 | 514.2 | B | 7.88 | 100 | — |
| II-3 | 524.2 | B | 8.24 | 100 | — |
| II-4 | 508.2 | B | 7.06 | 95 | — |
| II-5 | 631.2 | B | 7.85 | 100 | — |
| II-6 | 592.1 | B | 8.02 | 100 | — |
| II-7 | 544.2 | B | 8.31 | 100 | — |
| II-8 | 574.1 | B | 8.13 | 100 | — |
| II-9 | 617.2 | B | 7.73 | 100 | — |
| II-10 | 601.2 | B | 8.16 | 100 | — |
| II-11 | 601.2 | B | 8.15 | 90 | — |
| II-12 | 633.1 | B | 8.45 | 90 | — |
| II-13 | 573.2 | B | 7.58 | 100 | — |
| II-14 | 675.2 | B | 8.89 | 100 | — |
| II-15 | 575.2 | B | 7.11 | 100 | — |
| II-16 | 677.2 | B | 7.94 | 100 | — |
| II-17 | 675.2 | B | 8.88 | 100 | — |
| II-18 | 575.2 | B | 7.1 | 100 | — |
| II-19 | 599.1 | B | 7.37 | 99 | — |
| II-20 | 617.2 | B | 4.5 | 95 | — |
| II-21 | 631.1 | B | 7.76 | 100 | — |
| II-22 | 544.2 | B | 8.1 | 93 | — |
| II-23 | 600.3 | B | 9.43 | 100 | — |
| II-24 | 617.1 | B | 7.56 | 95 | — |
| II-25 | 617.1 | B | 7.56 | 100 | Y |
| II-26 | 516.1 | B | 7.25 | 95 | Y |
| II-27 | 530.2 | B | 7.58 | 90 | — |
| II-28 | 572.2 | B | 8.94 | 90 | — |
| II-29 | 574.2 | B | 7.59 | 100 | — |
| II-30 | 532.2 | B | 6.81 | 100 | — |
| II-31 | 546.2 | B | 4.42 | 90 | — |
| II-32 | 560.2 | B | 4.5 | 97 | — |
| II-33 | 527.2 | B | 4.71 | 100 | — |
| II-34 | 544.2 | B | 4.74 | 85 | — |
| II-35 | 550.1 | B | 4.7 | 100 | — |
| II-36 | 614 | B | 5.86 | 95 | — |
| II-37 | 631.2 | B | 5.21 | 95 | — |
| II-38 | 601.2 | B | 4.73 | 100 | — |
| II-39 | 535.2 | B | 8.95 | 100 | Y |
| II-40 | 634.2 | B | 11.53 | 100 | Y |
| II-41 | 548.2 | B | 9.02 | 100 | — |
| II-42 | 492.2 | B | 7.96 | 100 | — |

Example 14

ERK Inhibition Assay

Compounds are assayed for the inhibition of ERK2 by a spectrophotometric coupled-enzyme assay (Fox et al (1998) *Protein Sci* 7, 2249). In this assay, a fixed concentration of activated ERK2 (10 nM) is incubated with various concentrations of the compound in DMSO (2.5%) for 10 min. at 30° C. in 0.1 M HEPES buffer, pH 7.5, containing 10 mM $MgCl_2$, 2.5 mM phosphoenolpyruvate, 200 μM NADH, 150 μg/mL pyruvate kinase, 50 μg/mL lactate dehydrogenase, and 200 μM erktide peptide. The reaction is initiated by the addition of 65 μM ATP. The rate of decrease of absorbance at 340 nm is monitored, which indicates the extent of uninhibited enzyme present in the assay. The $IC_{50}$ is evaluated from the rate data as a function of inhibitor concentration.

Table 5 shows the results of the activity of selected compounds of this invention in the ERK2 inhibition assay. The compound numbers correspond to the compound numbers in Tables 1–3. Compounds having an activity designated as "A" provided a $K_i$ value below 1 micromolar; and compounds having an activity designated as "B" provided a $K_i$ value between 1 and 5 micromolar.

TABLE 5

ERK2 Inhibitory Activity of Selected Compounds

| Compound No. | Activity |
|---|---|
| II-1 | A |
| II-2 | A |
| II-3 | A |
| II-4 | A |
| II-5 | A |
| II-6 | A |
| II-7 | A |
| II-8 | A |
| II-9 | A |
| II-10 | A |
| II-11 | A |
| II-12 | A |
| II-13 | A |
| II-14 | A |
| II-15 | A |
| II-16 | A |
| II-17 | A |
| II-18 | A |
| II-19 | A |
| II-20 | A |
| II-21 | A |
| II-22 | A |
| II-23 | A |
| II-24 | A |
| II-25 | A |
| II-26 | A |
| II-27 | A |
| II-28 | A |
| II-29 | A |
| II-30 | A |
| II-31 | A |
| II-32 | A |
| II-33 | A |
| II-34 | A |
| II-35 | A |
| II-36 | A |
| II-37 | A |
| II-38 | A |
| II-39 | A |
| II-40 | B |
| II-41 | A |
| II-42 | A |
| II-52 | A |
| II-53 | A |
| II-54 | A |
| II-55 | A |
| II-56 | A |
| II-57 | A |
| II-58 | A |
| II-59 | A |
| II-60 | A |
| II-61 | A |
| II-62 | A |
| II-63 | A |
| II-64 | A |
| II-65 | A |
| II-66 | A |
| II-67 | A |
| II-68 | A |
| II-69 | A |
| II-70 | A |
| II-71 | A |
| II-72 | A |
| II-73 | A |
| II-74 | A |
| II-75 | A |
| II-76 | A |
| II-77 | A |
| II-78 | A |
| II-79 | A |
| II-80 | A |
| II-81 | A |
| II-82 | A |
| II-83 | A |
| II-84 | A |

TABLE 5-continued

ERK2 Inhibitory Activity of Selected Compounds

| Compound No. | Activity |
| --- | --- |
| II-85 | A |
| II-86 | A |

Example 15

ERK Inhibition Cell Proliferation Assay

Compounds may be assayed for the inhibition of ERK2 by a cell proliferation assay. In this assay, a complete media is prepared by adding 10% fetal bovine serum and penicillin/streptomycin solution to RPMI 1640 medium (JRH Biosciences). Colon cancer cells (HT-29 cell line) are added to each of 84 wells of a 96 well plate at a seeding density of 10,000 cells/well/150 µL. The cells are allowed to attach to the plate by incubating at 37° C. for 2 hours. A solution of test compound is prepared in complete media by serial dilution to obtain the following concentrations: 20 µM, 6.7 µM, 2.2 µM, 0.74 µM, 0.25 µM, and 0.08 µM. The test compound solution (50 µL) is added to each of 72 cell-containing wells. To the 12 remaining cell-containing wells, only complete media (200 µL) is added to form a control group in order to measure maximal proliferation. To the remaining 12 empty wells, complete media is added to form a vehicle control group in order to measure background. The plates are incubated at 37° C. for 3 days. A stock solution of $^3$H-thymidine (1 mCi/mL, New England Nuclear, Boston, Mass.) is diluted to 20 mCi/mL in RPMI medium then 20 µL of this solution is added to each well. The plates are further incubated at 37° C. for 8 hours then harvested and analyzed for $^3$H-thymidine uptake using a liquid scintillation counter.

Selected compounds of this invention that inhibit ERK in the colon cell proliferation assay, with an $IC_{50}$ of less than 10 µM include: II-7, II-21, II-24, II-25, and II-26.

Example 16

AKT Inhibition Assay:

Compounds were screened for their ability to inhibit AKT using a standard coupled enzyme assay (Fox et al., *Protein Sci.*, (1998) 7, 2249). Assays were carried out in a mixture of 100 mM HEPES 7.5, 10 mM MgCl2, 25 mM NaCl, 1 mM DTT and 1.5% DMSO. Final substrate concentrations in the assay were 170 µM ATP (Sigma Chemicals) and 200 µM peptide (RPRAATF, American Peptide, Sunnyvale, Calif.). Assays were carried out at 30° C. and 45 nM AKT. Final concentrations of the components of the coupled enzyme system were 2.5 mM phosphoenolpyruvate, 300 µM NADH, 30 pg/ML pyruvate kinase and 10 µg/ml lactate dehydrogenase.

An assay stock buffer solution was prepared containing all of the reagents listed above, with the exception of AKT, DTT, and the test compound of interest. 56 µl of the stock solution was placed in a 384 well plate followed by addition of 1 µl of 2 mM DMSO stock containing the test compound (final compound concentration 30 µM). The plate was pre-incubated for about 10 minutes at 30° C. and the reaction initiated by addition of 10 µl of enzyme (final concentration 45 nM) and 1 mM DTT. Rates of reaction were obtained using a BioRad Ultramark plate reader (Hercules, Calif.) over a 5 minute read time at 30° C. Compounds showing greater than 50% inhibition versus standard wells containing the assay mixture and DMSO without test compound were titrated to determine $IC_{50}$ values.

Selected compounds of this invention that inhibit AKT with an $IC_{50}$ of less than 12 µM include: II-6, II-7, II-11, II-13, II-15, II-17, II-18, II-22, II-24, II-25, II-40, II-41, II-52, II-53, II-54, II-55, II-56, II-67, II-68, II-69, II-70, II-71, II-72, II-73, II-74, II-75, II-76, II-77, II-78, II-79, II-80, II-81, II-82, II-83, II-84, II-85, and II-86.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

What is claimed is:

1. A method of treating or lessening the severity of a disease or condition selected from the group consisting of a cancer selected from breast cancer, ovarian cancer, cervical cancer, prostate cancer, testicular cancer, cancer of the genitourinary tract, esophogeal cancer, cancer of the larynx, glioblastoma, neuroblastoma, cancer of the stomach, skin cancer, keratoacanthoma, lung cancer, epidemoid carcinoma, large cell carcinoma, small cell carcinoma, lung adenocarcinoma, bone cancer, cancer of the colon, adenoma, pancreatic cancer, adenocarcinoma, thyroid cancer, follicular carcinoma, undifferentiated carcinoma, papillary carcinoma, seminoma, melanoma, sarcoma, bladder carcinoma, liver carcinoma, cancer of the biliary passages, kidney carcinoma, myeloid disorders, lymphoid disorders, Hodgkin's, hairy cell carcinoma, cancer of the buccal cavity or pharynx, lip cancer, tongue cancer, cancer of large intestine, rectal cancer, cancer of the brain and central nervous system, or leukemia; stroke; diabetes; hepatomegaly; a cardiovascular disease selected from restenosis, cardiomegaly, artherosclerosis, myocardial infarction, or congestive heart failure; cystic fibrosis; psoriasis; asthma; inflammation; neurodegenerative disease selected from Alzheimer's disease, Parkinson's disease amyotrophic lateral sclerosis, Huntington's disease, cerebral ischemia or neurodegenerative disease caused by traumatic injury, glutamate neurotoxicity or hypoxia; and conditions associated with organ transplantation, comprising the step of administering to said patient a composition comprising a compound of formula III-A, III-B, or III-C:

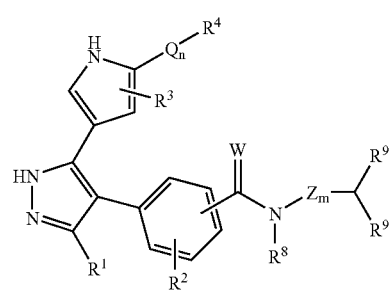

III-A

-continued

III-B

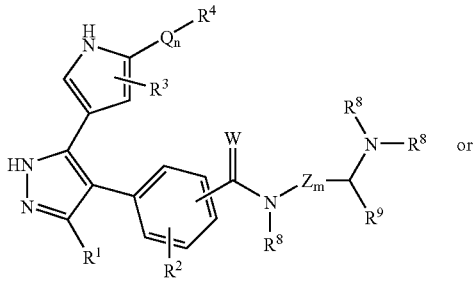

III-C

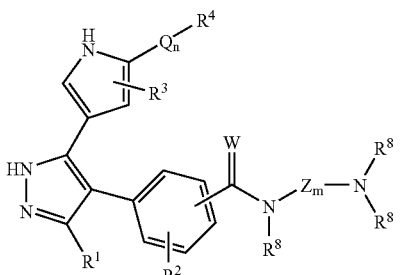

or a pharmaceutically acceptable salt thereof, wherein
W is $H_2$;
Z is an optionally substituted $C_1$–$C_4$ alkylidene chain; wherein 1 methylene unit is optionally replaced by —O—, —C(O)—, —C(O)C(O)—, —C(O)NH—, —C(O)NHNH—, —$CO_2$—, —OC(O)—, —$NHCO_2$—, —NHC(O)NH—, —OC(O)NH—, —NH—, —NHNH—, —NHCO—, —S—, —SO—, —$SO_2$—, —$SO_2$NH—, —$NHSO_2$—, or —$NHSO_2$NH—;
m is 0 or 1;
Q is an optionally substituted $C_1$–$C_6$ alkylidene chain, wherein up to two methylene units are replaced by —C(O)—, —C(O)C(O)—, —C(O)$NR^7$—, —C(O)$NR^7NR^7$—, —$CO_2$—, —OC(O)—, —$NR^7CO_2$—, —O—, —$NR^7$C(O)$NR^7$—, —OC(O)$NR^7$—, —$NR^7NR^7$—, —$NR^7$C(O)—, —S—, —SO—, —$SO_2$—, —$NR^7$—, —$SO_2NR^7$—, —$NR^7SO_2$—, or —$NR^7SO_2NR^7$—;
n is zero or one;
$R^1$ is hydrogen, R, fluoro, —CN, $N(R^7)_2$, $OR^7$, $NR^7C(O)R^7$, $NR^7C(O)N(R^7)_2$, $C(O)N(R^7)_2$, $SO_2R^7$, $NR^7SO_2R^7$, or $SO_2N(R^7)_2$;
each $R^2$ independently selected from R, OH, OR, SH, SR, nitro, $N(R^7)_2$, halogen, $CF_3$, or cyano;
$R^3$ is hydrogen, R, OH, OR, $N(R^7)_2$, fluoro, or CN;
$R^4$ is selected from —$(CH_2)_yR^6$, —$(CH_2)_yR^{10}$, —$(CH_2)_y$CH$(R^6)_2$, —$(CH_2)_y$CH$(R^{10})_2$, —$(CH_2)_y$CH$(R^{10})$CH$(R^6)_2$, —$(CH_2)_y$CH$(R^{10})(R^6)$, —$N(R^5)_2$, or —$NR^5(CH_2)_yN(R^5)_2$;
each R is independently selected from an optionally substituted group selected from $C_{1-6}$ aliphatic or $C_{6-10}$ aryl;
each $R^5$ is independently selected from R, —$(CH_2)_yR^6$, —$(CH_2)_y$CH$(R^6)_2$, $R^7$, —C(O)$R^7$, —$CO_2R^7$, —C(O)N$(R^7)_2$, or —$SO_2R^7$;
each y is independently 0–6;
each $R^6$ is independently selected from hydrogen, R, —$(CH_2)_y$R, —OH, —OR, —$CO_2$R, —$(CH_2)_yN(R^7)_2$, —$N(R^7)_2$, —$OR^7$, —$SR^7$, —$NR^7C(O)R^7$, —$NR^7C(O)$ $N(R^7)_2$, —C(O)$N(R^7)_2$, —$SO_2R^7$, —$NR^7SO_2R^7$, —C(O)$R^7$, —CN, or —$SO_2N(R^7)_2$;

each $R^7$ is independently selected from hydrogen or an optionally substituted $C_{1-6}$ aliphatic group;
each $R^8$ is independently selected from hydrogen, R, —$(CH_2)_yR^9$, —$(CH_2)_y$CH$(R^9)_2$, —$(CH_2)_y$C(O)$R^9$, $R^9$, or $R^7$;
each $R^9$ independently selected from hydrogen, R, —OH, —OR, —SR, —S(O)R, —$SO_2$R, —C(O)$R^6$, —$CO_2R^6$, $NR^2$, halo, cyano, or nitro;
each $R^{10}$ is independently selected from R, —$(CH_2)_w$ $OR^7$, —$(CH_2)_wN(R^5)_2$, or —$(CH_2)_wSR^7$; and
each w is independently 0–4;
provided that when $Q_n$-$R^4$ is

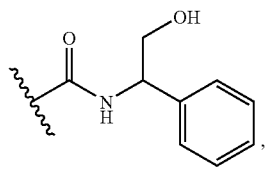

$R^1$ is H, and $R^3$ is H, and $R^2$ a meta substituent Cl, then $CH_2$—$N(R^8)$-$Z_m$-CH$(R^9)_2$ or $CH_2$—$N(R^8)$-$Z_m$-$N(R^8)_2$ is not a para substituent

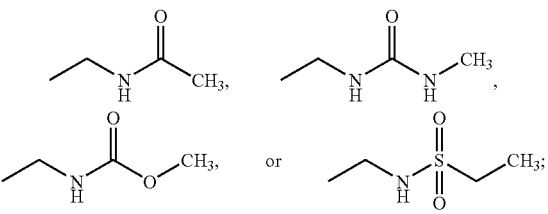

when $Q_n$—$R^4$ is

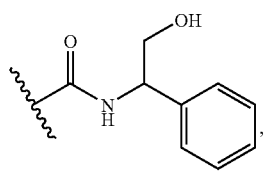

$R^1$ is $NH_2$, $R^2$ is a meta substituent Cl, and $R^3$ is H, then $CH_2$—$N(R^8)$-$Z_m$-CH$(R^9)_2$ is not a para substituent

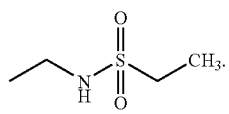

and a pharmaceutically acceptable carrier, adjuvant, or vehicle.

2. The method according to claim 1, wherein said method is used to treat a cardiovascular disease selected from restenosis, cardiomegaly, artherosclerosis, myocardial infarction, or congestive heart failure.

3. The method according to claim 1, wherein said method is used to treat a neurodegenerative disease selected from Alzheimer's disease, Parkinson's disease, amyotrophic lateral sclerosis, Huntington's disease, cerebral ischemia or neurodegenerative disease caused by traumatic injury, glutamate neurotoxicity or hypoxia.

4. The method according to claim 1, comprising the additional step of administering to said patient an additional therapeutic agent selected from an anti-proliferative agent selected from imatinib mesylate, adriamycin, dexamethasone, vincristine, cyclophosphamide, fluorouracil, topotecan, taxol, an interferon, or a platinum derivative; an anti-inflammatory agent selected from a corticosteroid, a TNF blocker. IL-1, azathioprine, cyclophosphamide, or sulfasalazine; an immunomodulatory agent selected from cyclosporin, tacrolimus, raparnycin, mycophenolate mofetil, an interferon, a corticosteroid, cyclophophamide, azathioprine, or sulfasalazine; a neurotrophic factor selected from acetylcholinesterase inhibitor, an MAO inhibitor, an interferon, an aniti-convulsant, an ion channel blocker, riluzole, or an anti-Parkinsoman agent; an agent for treating cardiovascular disease selected from a beta-blocker, an ACE inhibitor, a diuretic, a nitrate, a calcium channel blocker, or a statin; an agent for treating liver disease selected from 2, corticosteroid, cholestyramine, or an interferon; an agent for treating blood disorders selected from a corticosteroid, an anti-leukemic agent, or a growth factor; an agent for treating diabetes selected from insulin, an insulin analogue, an alpha glucosidase inhibitor, a biguanide, or an insulin sensitizer, or gamma globulin for treating an immunodeficiency disorder, wherein:

said additional therapeutic agent is appropriate for the disease being treated; and said additional therapeutic agent is administered together with said composition as a single dosage form or separately from said comfosition as part of a multiple dosage form.

5. The method of claim 1, wherein said compound is selected from a compound having the formula:

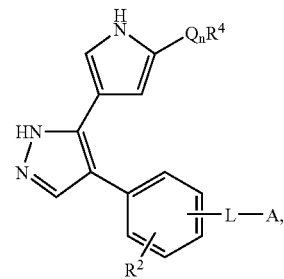

wherein each of $R^2$, -L-A, and $Q_n$-$R^4$ is as follows:

| No. | $R^2$ | —L—A | $Q_n$—$R^4$ |
|---|---|---|---|
| II-1 | 3-Cl | 4- ~N(H)-CH2-C(=O)-CH2-S(=O)2-CH3 | -C(=O)-N(H)-CH(CH2OH)-Ph |
| II-2 | 3-Cl | 4- ~N(H)-S(=O)2-CH3 | -C(=O)-N(H)-CH(CH2OH)-Ph |
| II-3 | 3-Cl | 4- ~N(H)-C(=O)-CH2CH2-O-CH3 | -C(=O)-N(H)-CH(CH2OH)-Ph |
| II-4 | 3-Cl | 4- ~N(H)-C(=O)-CH2CH2-OH | -C(=O)-N(H)-CH(CH2OH)-Ph |

-continued
| No. | R² | —L—A | Q$_n$—R⁴ |
|---|---|---|---|
| II-5 | 3-Cl | 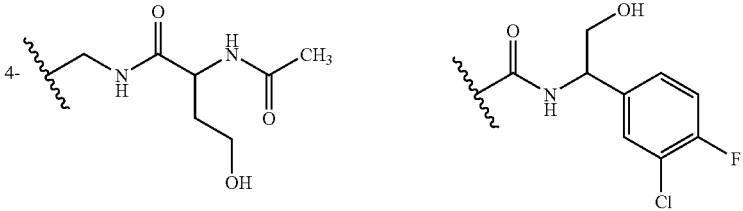 | 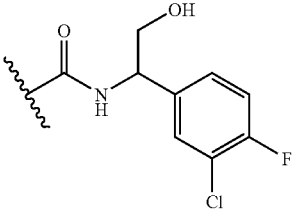 |
| II-6 | 3-Cl | 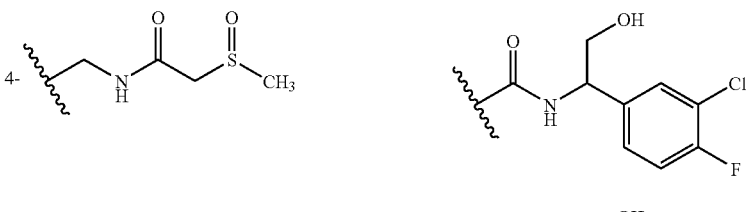 | 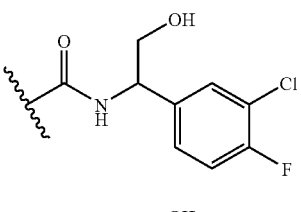 |
| II-7 | 3-Cl | 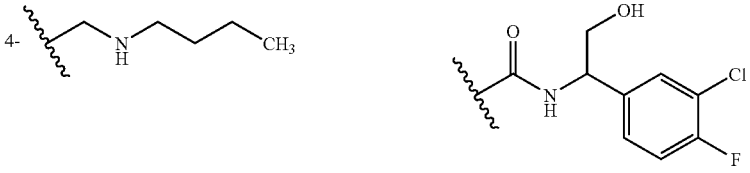 | 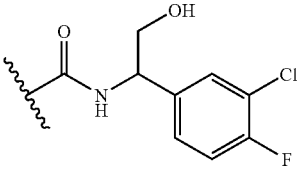 |
| II-8 | 3-Cl | 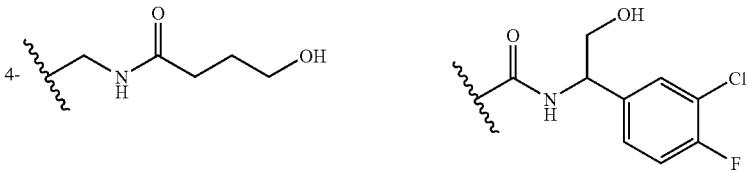 | 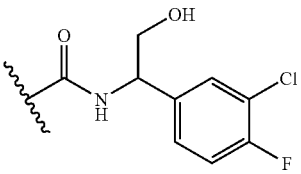 |
| II-9 | 3-Cl | 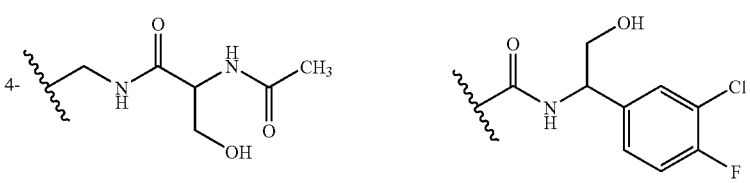 | 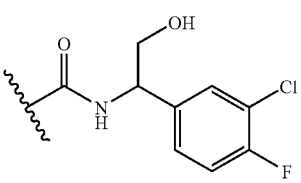 |
| II-10 | 3-Cl | 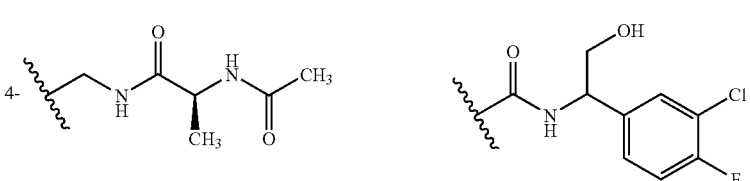 | 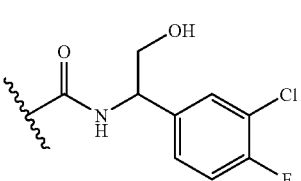 |
| II-11 | 3-Cl | 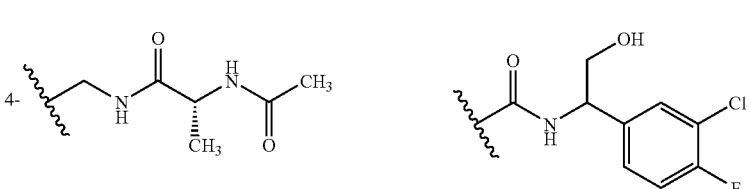 | 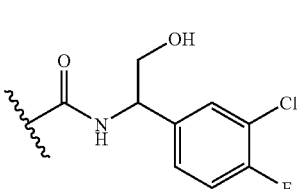 |
| II-12 | 3-Cl | 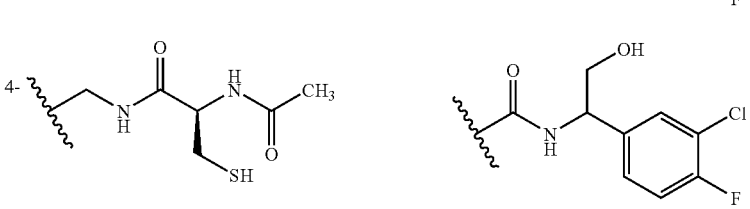 | 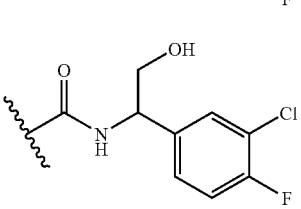 |

-continued
| No. | R² | —L—A | Qₙ—R⁴ |
|---|---|---|---|
| II-13 | 3-Cl | 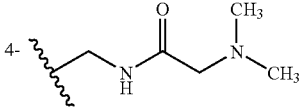 | 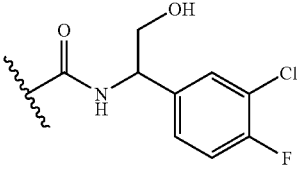 |
| II-14 | 3-Cl | 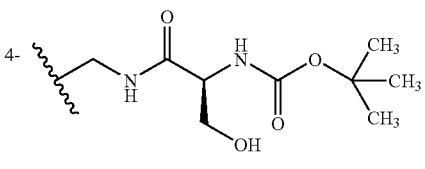 | 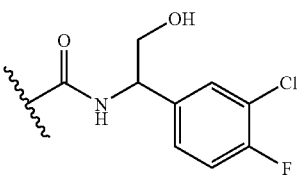 |
| II-15 | 3-Cl | 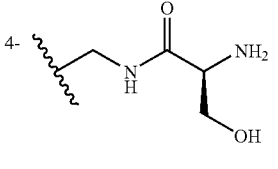 | 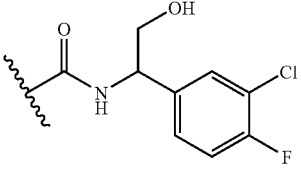 |
| II-16 | 3-Cl | 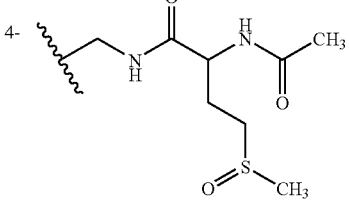 | 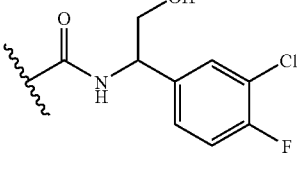 |
| II-17 | 3-Cl | 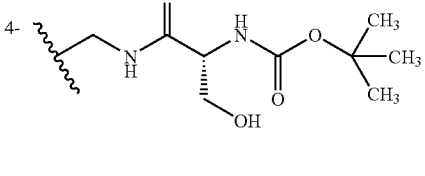 | 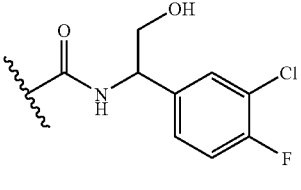 |
| II-18 | 3-Cl | 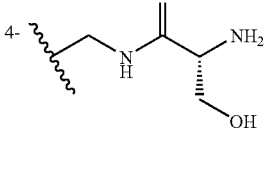 | 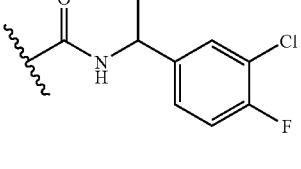 |
| II-19 | 3-Cl | 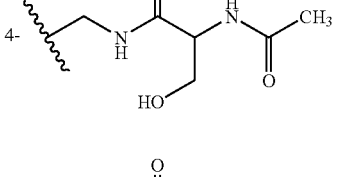 | 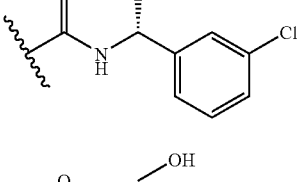 |
| II-20 | 3-Cl | 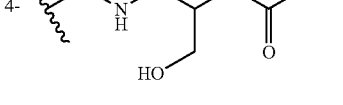 | 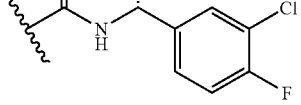 |

| No. | R² | —L—A | Qₙ—R⁴ |
|---|---|---|---|
| II-21 | 3-Cl | 4-CH₂-NH-C(=O)-CH(iPr)-NH-C(=O)-CH₃ (N-acetyl valinamide) | -C(=O)-NH-CH(CH₂OH)-(3-Cl,4-F-phenyl) |
| II-22 | 3-Cl | 4-CH₂-NH-CH₂CH₂CH₂CH₃ | -C(=O)-NH-CH(CH₂OH)-(3-Cl,4-F-phenyl) |
| II-23 | 3-Cl | 4-CH₂-N(CH₂CH₂CH₂CH₃)(CH₂CH₃) | -C(=O)-NH-CH(CH₂OH)-(3-Cl,4-F-phenyl) |
| II-24 | 3-Cl | 4-CH₂-NH-C(=O)-CH(CH₂OH)-NH-C(=O)-CH₃ (N-acetyl serinamide) | -C(=O)-NH-CH(CH₂OH)-(3-Cl,4-F-phenyl) |
| II-25 | 3-Cl | 4-CH₂-NH-C(=O)-CH(CH₂OH)-NH-C(=O)-CH₃ (N-acetyl serinamide, other stereoisomer) | -C(=O)-NH-CH(CH₂OH)-(3-Cl,4-F-phenyl) |
| II-26 | 3-Cl | 4-CH₂-NH-CH₃ | -C(=O)-NH-CH(CH₂OH)-(3-Cl,4-F-phenyl) |
| II-27 | 3-Cl | 4-CH₂-NH-CH₂CH₂CH₃ | -C(=O)-NH-CH(CH₂OH)-(3-Cl,4-F-phenyl) |
| II-28 | 3-Cl | 4-CH₂-N(CH₃)(CH₂CH₂CH₃) | -C(=O)-NH-CH(CH₂OH)-(3-Cl,4-F-phenyl) |

-continued
| No. | R² | —L—A | Qₙ—R⁴ |
|---|---|---|---|
| II-29 | 3-Cl | 4- 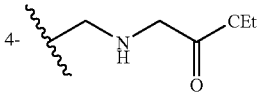 | 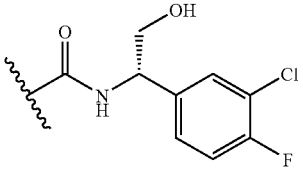 |
| II-30 | 3-Cl | 4- 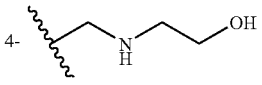 | 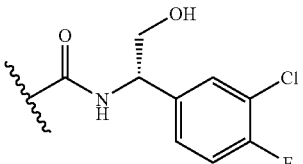 |
| II-31 | 3-Cl | 4- 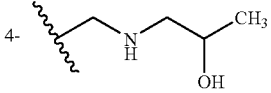 | 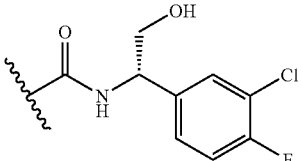 |
| II-32 | 3-Cl | 4- 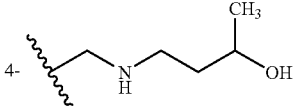 | 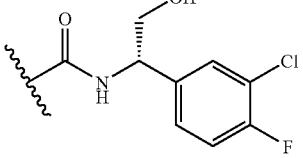 |
| II-33 | 3-Cl | 4- 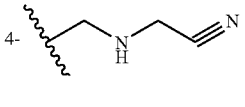 | 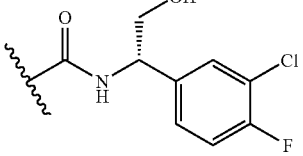 |
| II-34 | 3-Cl | 4- 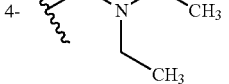 | 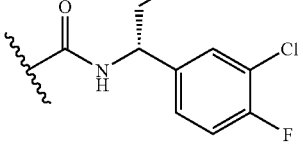 |
| II-35 | 3-Cl | 4- 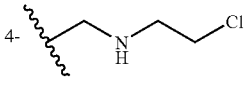 | 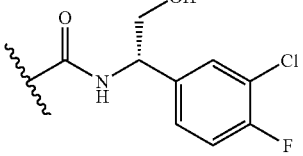 |
| II-36 | 3-Cl | 4- 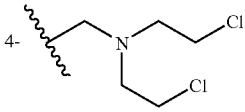 | 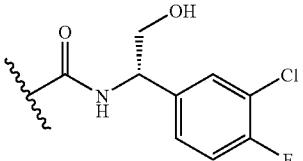 |

-continued

| No. | R² | —L—A | Qₙ—R⁴ |
|---|---|---|---|
| II-37 | 3-Cl | 4-, CH₂NH-CH₂CH₂-NH-C(=O)-O-C(CH₃)₃ | C(=O)-NH-CH(CH₂OH)-(3-Cl,4-F-phenyl) |
| II-38 | 3-Cl | 4-, CH₂NH-C(=O)-CH₂-N(CH₂CH₃)₂ | C(=O)-NH-CH(CH₂OH)-(3-Cl,4-F-phenyl) |
| II-39 | 3-Cl | 5-, CH₂NH-C(=O)-NH-CH₂CH₂CH₂CH₃ | C(=O)-NH-CH(CH₂OH)-phenyl |
| II-40 | 3-Cl | 5-, CH₂NH-C(=O)-NH-CH₂CH₂CH₂CH₃ | C(=O)-NH-CH(phenyl)-CH₂-O-C(=O)-NH-CH₂CH₂CH₂CH₃ |
| II-41 | 3-Cl | 5-, CH₂-N(CH₂CH₂CH₂CH₃)₂ | C(=O)-NH-CH(CH₂OH)-phenyl |
| II-42 | 3-Cl | 5-, CH₂NH-C(=O)-CH₂CH₃ | C(=O)-NH-CH(CH₂OH)-phenyl |
| II-43 | 3-Cl | 4-, CH₂-N(NH-CH₂CH₃)H | C(=O)-NH-CH(CH₂OH)-(3-Cl,4-F-phenyl) |
| II-44 | 3-Cl | 4-, CH₂CH₂CH₂-N(CH₂CH₃)-SO₂CH₃ | C(=O)-NH-CH(CH₂OH)-(3-Cl,4-F-phenyl) |

| No. | R² | —L—A | Qₙ—R⁴ |
|---|---|---|---|
| II-45 | 3,5-Cl | 4- CH₂N(CH₂CH₃)₂ | (S)-C(O)NH-CH(CH₂OH)-(3-Cl,4-F-phenyl) |
| II-46 | 3-Cl | 4- CH₂-NH-N(CH₃)-C(O)-CH(CH₃)-NHAc | (S)-C(O)NH-CH(CH₂OH)-(3-Cl,4-F-phenyl) |
| II-48 | 3-F-5-CF₃ | 4- CH₂-NH-C(O)-CH(NAc)-CH₂OH | (S)-C(O)NH-CH(CH₂OH)-(3-Cl,4-F-phenyl) |
| II-52 | 3-Cl | 4- CH₂-NH-CH(CH₃)-CH₂-C(O)-N(CH₃)₂ | (S)-C(O)NH-CH(CH₂OH)-(3-Cl,4-F-phenyl) |
| II-53 | 3-Cl | 4- CH₂-NH-CH₂-C(O)-CH₂CH₃ | (S)-C(O)NH-CH(CH₂OH)-(3-Cl,4-F-phenyl) |
| II-54 | 3-Cl | 4- CH₂-N(CH₃)-CH(CH₃)₂ | (S)-C(O)NH-CH(CH₂OH)-(3-Cl,4-F-phenyl) |
| II-55 | 3-Cl | 4- CH₂-NH-CH(CH₃)-C(O)-O-CH₂CH₃ | (S)-C(O)NH-CH(CH₂OH)-(3-Cl,4-F-phenyl) |
| II-56 | 3-Cl | 4- CH₂-NH-C(O)-CH(NH₂)-CH₂OH | (S)-C(O)NH-CH(CH₂OH)-(3-Cl,4-F-phenyl) |

| No. | R² | —L—A | Qₙ—R⁴ |
|---|---|---|---|
| II-57 | 3-CF₃ | 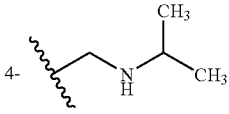 | 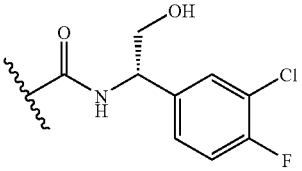 |
| II-58 | 3-CF₃ | 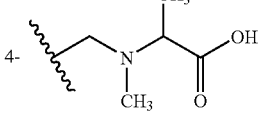 | 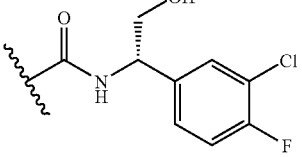 |
| II-59 | 3-CF₃ | 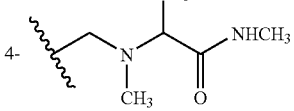 | 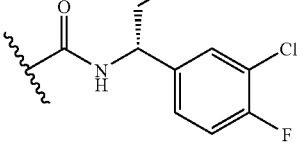 |
| II-60 | 3-CF₃ | 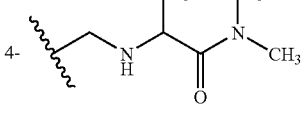 | 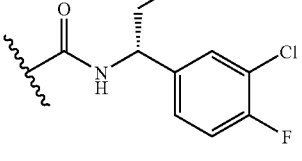 |
| II-61 | 3-CF₃ | 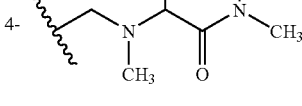 | 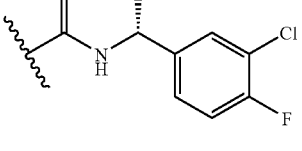 |
| II-62 | 3-CF₃ | 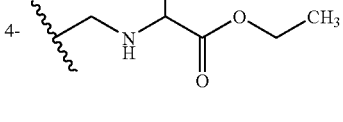 | 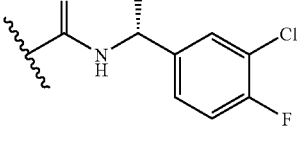 |
| II-63 | 3-Cl | 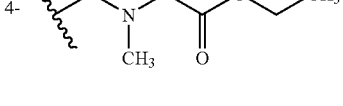 | 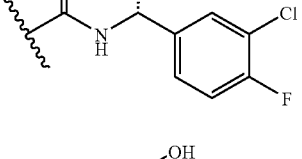 |
| II-64 | 3-CF₃ | 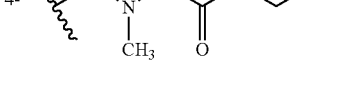 | 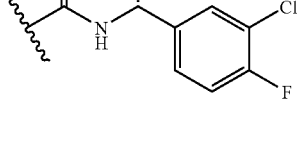 |

| No. | R² | —L—A | Qₙ—R⁴ |
|---|---|---|---|
| II-65 | 3-CF₃ | 4- with -NH-CH(CH₃)-C(=O)-NH-CH₃ | -C(=O)-NH-(S)-CH(CH₂OH)-(3-Cl,4-F-phenyl) |
| II-66 | 3-Cl | 4- with -NH-CH(CH₃)-C(=O)-N(CH₃)₂ | -C(=O)-NH-(S)-CH(CH₂OH)-(3-Cl,4-F-phenyl) |
| II-67 | 3-Cl | 4- with -NH-C(=O)-CH(NHCH₃)-CH₂OH | -C(=O)-NH-(S)-CH(CH₂OH)-(3-Cl,4-F-phenyl) |
| II-68 | 3-Cl | 4- with -NH-CH₂-CH₂-NH₂ | -C(=O)-NH-(S)-CH(CH₂OH)-(3-Cl,4-F-phenyl) |
| II-69 | 3-Cl | 4- with -NH-C(=O)-CH(NH₂)-CH₃ | -C(=O)-NH-(S)-CH(CH₂OH)-(3-Cl,4-F-phenyl) |
| II-70 | 3-Cl | 4- with -NH-CH(CH₃)₂ | -C(=O)-NH-(S)-CH(CH₂OH)-(3-Cl,4-F-phenyl) |
| II-71 | 3-Cl | 4- with -NH-CH₂-C(=O)-NH-CH₂CH₃ | -C(=O)-NH-(S)-CH(CH₂OH)-(3-Cl,4-F-phenyl) |
| II-72 | 3-Cl | 4- with -NH-CH(CH₃)-CH₂-C(=O)-O-CH₂CH₃ | -C(=O)-NH-(S)-CH(CH₂OH)-(3-Cl,4-F-phenyl) |

-continued
| No. | R² | —L—A | Qₙ—R⁴ |
|---|---|---|---|
| II-73 | 3-Cl | 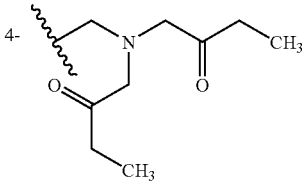 4- | 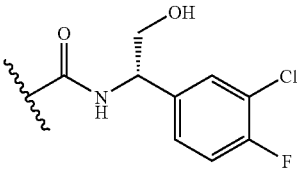 |
| II-74 | 3-Cl | 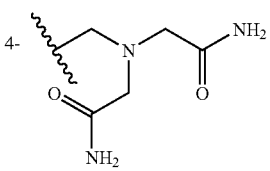 4- | 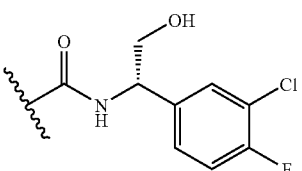 |
| II-75 | 3-Cl | 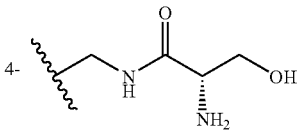 4- | 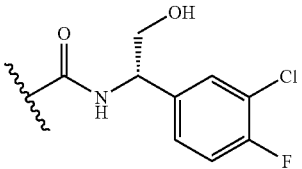 |
| II-76 | 3-Cl | 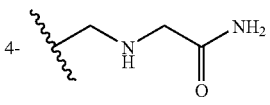 4- | 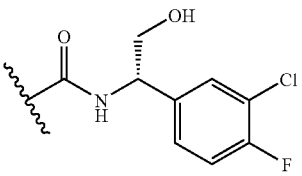 |
| II-77 | 3-Cl | 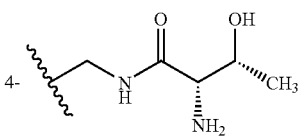 4- | 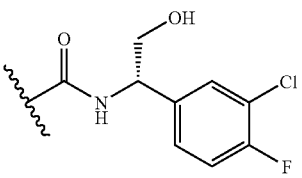 |
| II-78 | 3-Cl | 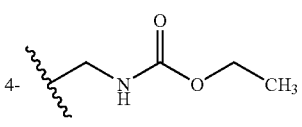 4- | 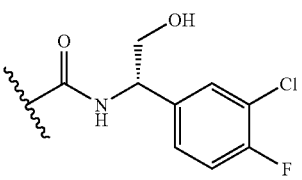 |
| II-79 | 3-Cl | 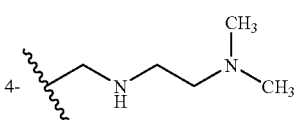 4- | 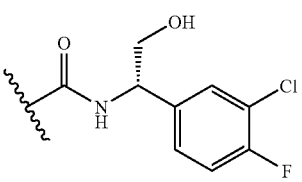 |

-continued
| No. | R² | —L—A | Qₙ—R⁴ |
|---|---|---|---|
| II-80 | 3-Cl | 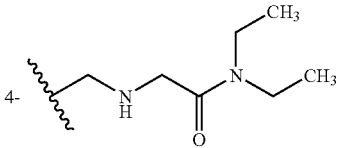 | 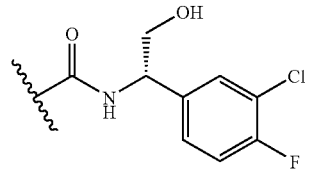 |
| II-81 | 3-Cl | 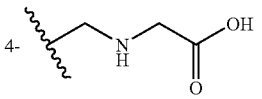 | 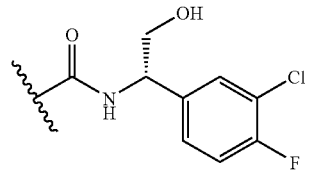 |
| II-82 | 3-Cl | 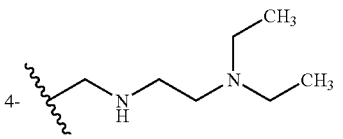 | 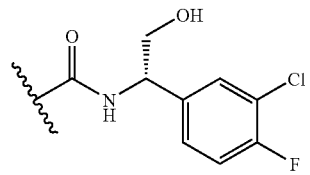 |
| II-83 | 3-Cl | 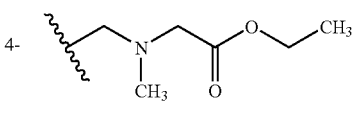 | 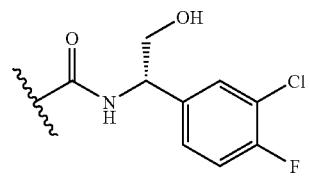 |
| II-84 | 3-Cl | 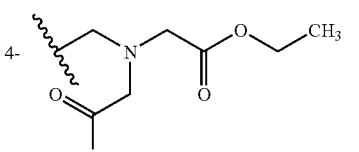 | 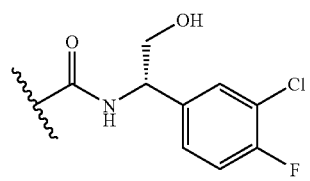 |
| II-85 | 3-Cl | 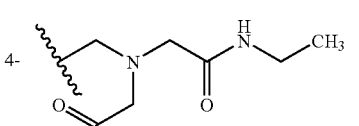 | 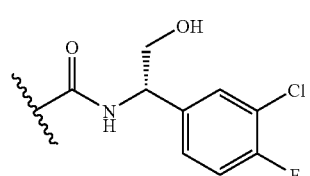 |
| II-86 | 3-Cl | 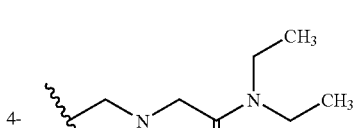 | 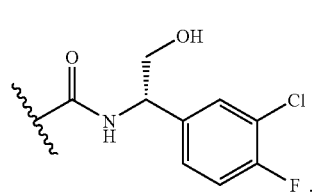 |

6. The method of claim 1, wherein said compound is selected from the following compounds:

| No. | Compound |
|---|---|
| I-1 | *(structure)* |
| I-2 | *(structure)* |
| I-3 | *(structure)* |
| I-4 | *(structure)* |
| I-5 | *(structure)* |
| I-6 | *(structure)* |

| No. | Compound |
|---|---|
| I-7 | 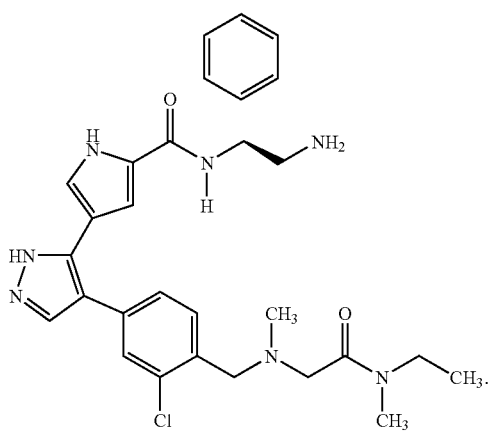 |

7. The method of claim 1, wherein said method is used to treat a cancer selected from breast cancer, ovarian cancer, cervical cancer, prostate cancer, testicular cancer, cancer of the genitourinary tract, cancer of the esophagus, cancer of the larynx, glioblastoma, neuroblastoma, stomach cancer, skin cancer, keratoacanthoma, lung cancer, epidermoid carcinoma, large cell carcinoma, small cell carcinoma, lung adenocarcinoma, bone cancer, colon cancer, adenoma, pancreatic cancer, adenocarcinoma, cancer of the thyroid, follicular carcinoma, undifferentiated carcinoma, papillary carcinoma, serninoma, melanoma, sarcoma, bladder carcinoma, liver carcinoma, cancer of the biliary passages, kidney carcinoma, myeloid disorders, lymphoid disorders, Hodgkin's disease, hairy cell carcinoma, cancer of the buccal cavity or pharynx, cancer of the lip, cancer of the tongue, cancer of the mouth, cancer of the pharynx, cancer of the small intestine, colorectal cancer, cancer of the large intestine, cancer of the rectum, brain cancer, cancer of the central nervous system, or leukemia.

* * * * *